(12) United States Patent
Gori

(10) Patent No.: US 12,319,895 B2
(45) Date of Patent: Jun. 3, 2025

(54) CLEANING COMPOSITIONS AND USES THEREOF

(71) Applicant: Novozymes A/S, Bagsvaerd (DK)

(72) Inventor: Klaus Gori, Dyssegaard (DK)

(73) Assignee: Novozymes A/S, Bagsvaerd (DK)

(*) Notice: Subject to any disclaimer, the term of this patent is extended or adjusted under 35 U.S.C. 154(b) by 0 days.

(21) Appl. No.: 18/342,030

(22) Filed: Jun. 27, 2023

(65) Prior Publication Data

US 2023/0340368 A1    Oct. 26, 2023

Related U.S. Application Data

(62) Division of application No. 17/188,017, filed on Mar. 1, 2021, now Pat. No. 11,739,287, which is a division of application No. 16/500,424, filed as application No. PCT/EP2018/056730 on Mar. 16, 2018, now Pat. No. 10,968,416.

(30) Foreign Application Priority Data

Apr. 6, 2017    (EP) .................................... 17165343

(51) Int. Cl.
    C12N 9/22    (2006.01)
    C11D 3/386    (2006.01)

(52) U.S. Cl.
    CPC ...... *C11D 3/38636* (2013.01); *C11D 3/38645* (2013.01); *C11D 2111/12* (2024.01)

(58) Field of Classification Search
    CPC ....... C12N 9/22; C12N 9/2437; C12N 9/2417
    See application file for complete search history.

(56) References Cited

U.S. PATENT DOCUMENTS 11,739,287 B2 *  8/2023  Gori ................... C11D 3/38645
                                                    435/194
2020/0199498 A1    6/2020  Gori

FOREIGN PATENT DOCUMENTS

| WO | 2014/087011 A1 | 6/2014 |
|---|---|---|
| WO | 2014/124927 A2 | 8/2014 |
| WO | 2015/155350 A1 | 10/2015 |
| WO | 2015/155351 A1 | 10/2015 |
| WO | 2015/166075 A1 | 11/2015 |
| WO | 2015/181286 A1 | 12/2015 |
| WO | 2015/181287 A1 | 12/2015 |
| WO | 2015/181827 A1 | 12/2015 |
| WO | 2016/162556 A1 | 10/2016 |
| WO | 2016/162558 A1 | 10/2016 |
| WO | 2017/001471 A1 | 1/2017 |
| WO | 2017/001472 A1 | 1/2017 |
| WO | 2017/059802 A1 | 4/2017 |
| WO | 2017/060475 A2 | 4/2017 |
| WO | 2018/011277 A1 | 1/2018 |

OTHER PUBLICATIONS

Yoon et al., 2005, International Journal of Systematic and Evolutionary Microbiology 55, 733-736.
Yoon et al., 2014, EBI Accession No. UNIPROT:A0A084H293.

* cited by examiner

*Primary Examiner* — Tekchand Saidha
(74) *Attorney, Agent, or Firm* — Elias Lambiris

(57) ABSTRACT

The present invention relates to compositions such as cleaning compositions comprising a mix of enzymes. The invention further relates, use of compositions comprising such enzymes in cleaning processes.

17 Claims, No Drawings

Specification includes a Sequence Listing.

CLEANING COMPOSITIONS AND USES THEREOF

CROSS-REFERENCE TO RELATED APPLICATIONS

This application is a divisional of U.S. application Ser. No. 17/188,017 filed Mar. 1, 2021, now U.S. Pat. No. 11,739,287, which is a divisional of U.S. application Ser. No. 16/500,424 filed Oct. 3, 2019, now U.S. Pat. No. 10,968,416, which is a 35 U.S.C. 371 national application of international application no. PCT/EP2018/056730 filed Mar. 16, 2018, which claims priority under 35 U.S.C. 119 of European application no. 17165343.9 filed Apr. 6, 2017. The disclosure of each application is fully incorporated herein by reference.

REFERENCE TO A SEQUENCE LISTING

This application contains a Sequence Listing in computer readable form, which is hereby incorporated by reference in its entirety. The electronic sequence listing was created on Jun. 29, 2023, is named SQ.xml, and is 96,875 bytes in size.

BACKGROUND OF THE INVENTION

The present invention relates to compositions such as cleaning compositions comprising a mix of enzymes. The invention further relates, use of compositions comprising such enzymes in cleaning processes and/or for deep cleaning of biofilm soiling, methods for removal or reduction of biofilm related soiling.

DESCRIPTION OF THE RELATED ART

Enzymes have been used in detergents for decades. Usually a cocktail of various enzymes is added to detergent compositions. The enzyme cocktail often comprises various enzymes, wherein each enzyme targets it specific substrate, e.g., amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of soiling may be organic matter, such as biofilm, EPS, etc. Organic matter composes different molecules such as polysaccharides, extracellular DNA (eDNA), and proteins. Some organic matter composes an extracellular polymeric matrix, which may be sticky or glueing, which when present on textile, attracts soils and may course redeposition or backstaining of soil resulting in a greying of the textile. Additionally, organic matters such as biofilms often cause malodor issue as various malodor molecules can be adhered by the polysaccharides, extracellular DNA (eDNA), and proteins in the complex extracellular matrix and be slowly released out to cause consumer noticeable malodor issue. There is still a need for cleaning compositions, which effectively prevent, reduce or remove components of organic stains, e.g., biofilm, an effect described in the present application as "deep cleaning". The present invention provides new compositions fulfilling such need.

SUMMARY OF THE INVENTION

A first aspect of the present invention, relates to a cleaning composition comprising a DNase, at least one carbohydrase and a cleaning component, wherein the carbohydrase is a cellulase, an amylase, a mannanase or a xylanase. Another aspect of the invention relates to a cleaning composition comprising at least 0.001 ppm DNase and at least 0.001 ppm carbohydrase and a cleaning component, wherein the cleaning component is selected from
  a. 0.1 to 15 wt. %, e.g., from about 1% to about 40% of at least one a surfactant;
  b. 0.5 to 20 wt. %, e.g., from about 5% to about 50% of at least one builder; and
  c. 0.01 to 10 wt. %, e.g., from about 1% to about 20% of at least one bleach component.

The invention further relates to the use of a composition for deep cleaning of an item, wherein the item is a textile or a surface. The invention further relates to the use of a cleaning composition comprising a DNase, at least one carbohydrase and a cleaning component, wherein the carbohydrase is a cellulase, an amylase, a mannanase or a xylanase. The invention further relates to a method of formulating a cleaning composition comprising adding a DNase, a carbohydrase and at least one cleaning component. The invention further relates to a kit intended for deep cleaning, wherein the kit comprises a solution of an enzyme mixture comprising a DNase and a carbohydrase, wherein the carbohydrase is a cellulase, an amylase, a mannanase or a xylanase. The invention further relates to a method of deep cleaning an item, comprising the steps of: a) contacting the item with a cleaning composition comprising a DNase, at least one carbohydrase and a cleaning component, wherein the carbohydrase is a cellulase, an amylase, a mannanase or a xylanase; and b) optionally rinsing the item, wherein the item is preferably a textile. The invention further relates to a method of deep cleaning of an item, comprising the steps of: a) contacting the item with a solution comprising an enzyme mixture comprising a DNase and a carbohydrase and optionally a protease; and a cleaning component, wherein the cleaning component is selected from 0.1 to 15 wt. %, e.g., from about 1% to about 40% of at least one a surfactant; 0.5 to 20 wt. %, e.g., from about 5% to about 50% of at least one builder; and 0.01 to 10 wt. %, e.g., from about 1% to about 20% of at least one bleach component; and b) optionally rinsing the item, wherein the item is preferably a textile.

DETAILED DESCRIPTION OF THE INVENTION

Various enzymes are applied in cleaning processes each targeting specific types of soiling such as protein, starch and grease soiling. Enzymes are now standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of staining due to the complex nature of such organic matters. None of the commercially available cleaning compositions effectively remove or reduce EPS and/or biofilm related stains. Biofilm may be produced when a group of microorganisms' cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as eDNA, lipids and other organic substances.

Organic matter like biofilm may be sticky or glueing, which when present on textile, may give rise to redeposition or backstaining of soil resulting in a greying of the textile. Another drawback of organic matter, e.g., biofilm is the malodor as various malodor related molecules are often associated with organic matter, e.g., biofilm. Further, when dirty laundry items are washed together with less dirty laundry items the dirt present in the wash liquor tend to stick to organic matter, e.g., biofilm or biofilm components as a result, hereof the laundry item is more "soiled" after wash than before wash. This is effect may also be termed redeposition.

The compositions of the invention comprise a blend of DNase and a carbohydrase, wherein the carbohydrase is a cellulase, an amylase, a mannanase or a xylanase and effectively reduce or remove organic components, such as protein and DNA from surfaces such as textiles and hard surfaces, e.g., dishes.

The compositions of the invention comprise a blend of DNase and a carbohydrase, wherein the carbohydrase is a cellulase, an amylase, a mannanase or a xylanase and effectively reduce or limit redeposition when applied in, e.g., laundry process.

The compositions of the invention comprise a blend of DNase and a carbohydrase, wherein the carbohydrase is a cellulase, an amylase, a mannanase or a xylanase and effectively reduce or limit malodor of, e.g., textiles or hard surfaces such as dishes.

The compositions of the invention comprise a blend of DNase and a carbohydrase, wherein the carbohydrase is a cellulase, an amylase, a mannanase or a xylanase and improve whiteness of textile.

A composition of the invention is preferably a cleaning composition, the composition of the invention comprises at least one DNase and at least one a carbohydrase, wherein the carbohydrase is a cellulase, an amylase, a mannanase or a xylanase. Examples of useful DNases and carbohydrases are mentioned below in the sections "Polypeptides having DNase activity" and "Polypeptides having mannanase, cellulase, xylanase or amylase activity" respectively.

Polypeptides Having DNase Activity

The term "DNase" means a polypeptide with DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endodeoxyribonucleases cleaves or cut within the DNA backbone. A DNase may cleave only double-stranded DNA or may cleave double stranded and single stranded DNA. The term "DNases" and the expression "a polypeptide with DNase activity" are used interchangeably throughout the application. For purposes of the present invention, DNase activity is determined according to the procedure described in the Assay I.

Preferably, the DNase is selected from any of the enzyme classes E.C.3.1, preferably E.C.3.1.21, e.g., such as E.C.3.1.21.X, where X=1, 2, 3, 4, 5, 6, 7, 8 or 9, or, e.g., Deoxyribonuclease I, Deoxyribonuclease IV, Type I site-specific deoxyribonuclease, Type II site-specific deoxyribonuclease, Type III site-specific deoxyribonuclease, CC-preferring endo-deoxyribonuclease, Deoxyribonuclease V, T (4) deoxyribonuclease II, T (4) deoxyribonuclease IV or E.C.3.1.22.Y where Y=1, 2, 4 or 5, e.g., Deoxyribonuclease II, *Aspergillus* deoxyribonuclease K (1), Crossover junction endo-deoxyribonuclease, Deoxyribonuclease X.

Preferably, the polypeptide having DNase activity is obtained from a microorganism and the DNase is a microbial enzyme. The DNase is preferably of fungal or bacterial origin.

The DNase may be obtainable from *Bacillus* e.g., *Bacillus licheniformis, Bacillus subtilis, Bacillus* sp-62451, *Bacillus horikoshii, Bacillus* sp-62451, *Bacillus* sp-16840, *Bacillus* sp-62668, *Bacillus* sp-13395, *Bacillus horneckiae, Bacillus* sp-11238, *Bacillus cibi, Bacillus idriensis, Bacillus* sp-62520, *Bacillus* sp-16840, *Bacillus* sp-62668, *Bacillus algicola, Bacillus vietnamensis, Bacillus hwajinpoensis, Bacillus indicus, Bacillus marisflavi, Bacillus luciferensis, Bacillus* sp. SA2-6.

The DNase may also be obtained from any of the following *Pyrenochaetopsis* sp., *Vibrissea flavovirens, Setosphaeria rostrate, Endophragmiella valdina, Corynespora cassiicola, Paraphoma* sp. XZ1965, *Monilinia fructicola, Curvularia lunata, Penicillium reticulisporum, Penicillium quercetorum, Setophaeosphaeria* sp., *Alternaria, Alternaria* sp. XZ2545, *Trichoderma reesei, Chaetomium thermophilum, Scytalidium thermophilum, Metapochonia suchlasporia, Daldinia fissa, Acremonium* sp. XZ2007, *Acremonium* sp. XZ2414, *Acremonium dichromosporum, Sarocladium* sp. XZ2014, *Metarhizium* sp. HNA15-2, *Isaria tenuipes Scytalidium circinatum, Metarhizium lepidiotae, Thermobispora bispora, Sporormia fimetaria, Pycnidiophora* cf. *dispera*, Enviromental sample D, Enviromental sample O, Clavicipitaceae sp-70249, *Westerdykella* sp. AS85-2, *Humicolopsis cephalosporioides, Neosartorya massa, Roussoella intermedia, Pleosporales, Phaeosphaeria* or *Didymosphaeria futilis*.

The DNases to be used in a composition of the invention preferable belong to the NUC1 group of DNases. The NUC1 group of DNases comprises polypeptides which in addition to having DNase activity, may comprise one or more of the motifs [T/D/S][G/N]PQL, [F/L/Y/I]A[N/R]D[L/I/P/V], or C[D/N]T[A/R]. One embodiment of the invention relates to a composition comprising a carbohydrase, selected from cellulases, amylases, mannanases and xylanases, and polypeptides having DNase activity, wherein the polypeptides comprises one or more of the motifs [T/D/S][G/N]PQL, [F/L/Y/I]A[N/R]D[L/I/P/V] or C[D/N]T[A/R].

The DNases preferably comprises a NUC1_A domain [D/Q][I/V]DH. In addition to comprising any of the domain motifs [T/D/S][G/N]PQL, [F/L/Y/I]A[N/R]D[L/I/P/V] or C[D/N]T[A/R] the polypeptides having DNase activity, to be used in a composition of the invention, may comprise the NUC1_A domain and may share the common motif [D/Q][I/V]DH. One embodiment the invention relates to compositions comprising a carbohydrase, selected from cellulases, amylases, mannanases and xylanases, and polypeptides, which comprises one or more motifs selected from the motifs [T/D/S][G/N]PQL, [F/L/Y/I]A[N/R]D[L/I/P/V], C[D/N]T[A/R] and [D/Q][I/V]DH, wherein the polypeptides have DNase activity.

The DNases to be added to a composition of the invention preferably belong to the group of DNases comprised in the GYS-clade, which are group of DNases on the same branch of a phylogenetic tree having both structural and functional similarities. These NUC1 and/or NUC1_A DNases comprise the conservative motifs [D/M/L][S/T]GYSR[D/N] (SEQ ID NO: 73) or ASXNRSKG (SEQ ID NO: 74) and share similar structural and functional properties. The DNases of the GYS-clade are preferably obtained from *Bacillus* genus.

One embodiment of the invention relates to a composition comprising a carbohydrase, selected from cellulases, amylases, mannanases and xylanases, a polypeptide of the GYS clade having DNase activity, optionally wherein the polypeptide comprise one or both of the motifs [D/M/L][S/T]GYSR[D/N] (SEQ ID NO: 73), ASXNRSKG (SEQ ID NO: 74) and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 24, and y) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 25.

Polypeptides having DNase activity and which comprise the GYS-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the GYS-clade DNases are particularly effective in preventing redeposition when laundering an item such as textile.

In one embodiment the DNases to be added in a composition of the invention preferably belong to the group of DNases comprised in the NAWK-clade, which are NUC1 and NUC1_A DNases, which may further comprise the conservative motifs [V/I]PL[S/A]NAWK (SEQ ID NO: 75) or NPQL (SEQ ID NO: 76).

One embodiment of the invention relates to a composition comprising a carbohydrase selected from a cellulase, an amylase, a mannanase or a xylanase, and a polypeptide of the NAWK-clade having DNase activity, optionally wherein the polypeptide comprise one or both of the motifs [V/I]PL[S/A]NAWK (SEQ ID NO: 75) or NPQL (SEQ ID NO: 76) and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 31, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 32, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 33, i) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 34, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 35, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 36, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 37, and m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 38.

Polypeptides having DNase activity and which comprise the NAWK-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the NAWK-clade DNases are particularly effective in preventing redeposition when laundering an item such as textile.

The DNases to be added in a composition of the invention preferably belong to the group of DNases comprised in the KNAW-clade, which are NUC1 and NUC1_A DNases which may further comprise the conservative motifs P[Q/E]L[W/Y] or [K/H/E]NAW.

One embodiment of the invention relates to a composition comprising a carbohydrase, selected from a cellulase, an amylase, a mannanase or a xylanase, and a polypeptide of the KNAW clade having DNase activity, optionally wherein the polypeptide comprise one or both of the motifs P[Q/E]L[W/Y] or [K/H/E]NAW, and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 39, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 40, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 41, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 42, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 43 f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 44, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 45, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 46, i) a polypeptide having at least 60%, at least 65%, at least 70%, at least 75%, at least 80%, at least 85%, at least 90%, at least 95%, at least 98% or at least 100% sequence identity to the polypeptide shown in SEQ ID NO: 47, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 48, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 49, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 50, and m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 51.

Polypeptides having DNase activity and which comprise the KNAW-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the KNAW-clade DNases are particularly effective in preventing redeposition when laundering an item such as textile.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62451 and having a sequence identity to the polypeptide shown in SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 1.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 2.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62520 and having a sequence identity to the polypeptide shown in SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 3.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62520 and having a sequence identity to the polypeptide shown in SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 4.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 5.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 6.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-16840 and having a sequence identity to the polypeptide shown in SEQ ID NO: 7 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 7.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-16840 and having a sequence identity to the polypeptide shown in SEQ ID NO: 8 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 8.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62668 and having a sequence identity to the polypeptide shown in SEQ ID NO: 9 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 9.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-13395 and having a sequence identity to the polypeptide shown in SEQ ID NO: 10 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 10.

In some embodiments, the present invention relates to compositions comprising a carbohydrase, selected from cellulases, amylases, mannanases and xylanases, and a polypeptide obtainable from *Bacillus*, e.g., obtainable from *Bacillus horneckiae* and having a sequence identity to the polypeptide shown in SEQ ID NO: 11 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 11.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-11238 and having a sequence identity to the polypeptide shown in SEQ ID NO: 12 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 12.

In some embodiments, the present invention relates to compositions comprising a carbohydrase, selected from cellulases, amylases, mannanases and xylanases, and a polypeptide obtainable from *Bacillus*, e.g., obtainable from *Bacillus cibi* and having a sequence identity to the polypeptide shown in SEQ ID NO: 13 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 13.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-18318 and having a sequence identity to the polypeptide shown in SEQ ID NO: 14 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 14.

In some embodiments, the present invention relates to compositions comprising a carbohydrase, selected from cellulases, amylases, mannanases and xylanases, and a polypeptide obtainable from *Bacillus*, e.g., obtainable from *Bacillus idriensis* and having a sequence identity to the polypeptide shown in SEQ ID NO: 15 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 15.

In some embodiments, the present invention relates to compositions comprising a carbohydrase, selected from cellulases, amylases, mannanases and xylanases, and a polypeptide obtainable from *Bacillus*, e.g., obtainable from *Bacillus algicola* having a sequence identity to the polypeptide shown in SEQ ID NO: 16 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 16.

In some embodiments, the present invention relates to compositions comprising a carbohydrase, selected from cellulases, amylases, mannanases and xylanases, and a polypeptide obtainable from Enviromental sample J and having a sequence identity to the polypeptide shown in SEQ ID NO: 17 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 17.

In some embodiments, the present invention relates to compositions comprising a carbohydrase, selected from cellulases, amylases, mannanases and xylanases, and a polypeptide obtainable from *Bacillus*, e.g., obtainable from *Bacillus vietnamensis* and having a sequence identity to the polypeptide shown in SEQ ID NO: 18 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 18.

In some embodiments, the present invention relates to compositions comprising a carbohydrase, selected from cellulases, amylases, mannanases and xylanases, and a polypeptide obtainable from *Bacillus*, e.g., obtainable from *Bacillus hwajinpoensis* and having a sequence identity to the polypeptide shown in SEQ ID NO: 19 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 19.

In some embodiments, the present invention relates to compositions comprising a carbohydrase, selected from cellulases, amylases, mannanases and xylanases, and a polypeptide obtainable from *Paenibacillus mucilaginosus* and having a sequence identity to the polypeptide shown in SEQ ID NO: 20 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 20.

In some embodiments, the present invention relates to compositions comprising a carbohydrase, selected from cellulases, amylases, mannanases and xylanases, and a polypeptide obtainable from *Bacillus*, e.g., obtainable from *Bacillus indicus* and having a sequence identity to the polypeptide shown in SEQ ID NO: 21 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 21.

In some embodiments, the present invention relates to compositions comprising a carbohydrase, selected from cellulases, amylases, mannanases and xylanases, and a polypeptide obtainable from *Bacillus*, e.g., obtainable from *Bacillus marisflavi* and having a sequence identity to the polypeptide shown in SEQ ID NO: 22 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 22.

In some embodiments, the present invention relates to compositions comprising a carbohydrase, selected from cellulases, amylases, mannanases and xylanases, and a polypeptide obtainable from *Bacillus*, e.g., obtainable from *Bacillus luciferensis* and having a sequence identity to the polypeptide shown in SEQ ID NO: 23 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 23.

In some embodiments, the present invention relates to compositions comprising a carbohydrase, selected from cellulases, amylases, mannanases and xylanases, and a polypeptide obtainable from *Bacillus*, e.g., obtainable from *Bacillus marisflavi* and having a sequence identity to the polypeptide shown in SEQ ID NO: 24 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 24.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp. SA2-6 and having a sequence identity to the polypeptide shown in SEQ ID NO: 25 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 25.

In some embodiments, the present invention relates to compositions comprising a carbohydrase, selected from cellulases, amylases, mannanases and xylanases, and a polypeptide obtainable from *Pyrenochaetopsis* sp. and having a sequence identity to the polypeptide shown in SEQ ID NO: 26 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 26.

In some embodiments, the present invention relates to compositions comprising a carbohydrase, selected from cellulases, amylases, mannanases and xylanases, and a polypeptide obtainable from *Vibrissea flavovirens* and having a sequence identity to the polypeptide shown in SEQ ID NO: 27 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 27.

In some embodiments, the present invention relates to compositions comprising a carbohydrase, selected from cellulases, amylases, mannanases and xylanases, and a polypeptide obtainable from *Setosphaeria* rostrate and having a sequence identity to the polypeptide shown in SEQ ID NO: 28 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 28.

In some embodiments, the present invention relates to compositions comprising a carbohydrase, selected from cellulases, amylases, mannanases and xylanases, and a polypeptide obtainable from *Endophragmiella valdina* and having a sequence identity to the polypeptide shown in SEQ ID NO: 29 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 29.

In some embodiments, the present invention relates to compositions comprising a carbohydrase, selected from cellulases, amylases, mannanases and xylanases, and a polypeptide obtainable from *Corynespora cassiicola* and having a sequence identity to the polypeptide shown in SEQ ID NO: 30 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 30.

In some embodiments, the present invention relates to compositions comprising a carbohydrase, selected from cellulases, amylases, mannanases and xylanases, and a polypeptide obtainable from *Paraphoma* sp. XZ1965 and having a sequence identity to the polypeptide shown in SEQ ID NO: 31 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 31.

In some embodiments, the present invention relates to compositions comprising a carbohydrase, selected from cellulases, amylases, mannanases and xylanases, and a polypeptide obtainable from *Monilinia fructicola* and having a sequence identity to the polypeptide shown in SEQ ID NO: 32 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 32.

In some embodiments, the present invention relates to compositions comprising a carbohydrase, selected from cellulases, amylases, mannanases and xylanases, and a polypeptide obtainable from *Curvularia lunata* and having a sequence identity to the polypeptide shown in SEQ ID NO: 33 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 33.

In some embodiments, the present invention relates to compositions comprising a carbohydrase, selected from cellulases, amylases, mannanases and xylanases, and a polypeptide obtainable from *Penicillium reticulisporum* and having a sequence identity to the polypeptide shown in SEQ ID NO: 34 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 34.

In some embodiments, the present invention relates to compositions comprising a carbohydrase, selected from cellulases, amylases, mannanases and xylanases, and a polypeptide obtainable from *Penicillium quercetorum* and having a sequence identity to the polypeptide shown in SEQ ID NO: 35 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 35.

In some embodiments, the present invention relates to compositions comprising a carbohydrase, selected from cellulases, amylases, mannanases and xylanases, and a polypeptide obtainable from *Setophaeosphaeria* sp. and having a sequence identity to the polypeptide shown in SEQ ID NO: 36 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 36.

In some embodiments, the present invention relates to compositions comprising a carbohydrase, selected from cellulases, amylases, mannanases and xylanases, and a polypeptide obtainable from *Alternaria* sp. XZ2545 and having a sequence identity to the polypeptide shown in SEQ ID NO: 37 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 37.

In some embodiments, the present invention relates to compositions comprising a carbohydrase, selected from cellulases, amylases, mannanases and xylanases, and a polypeptide obtainable from *Alternaria* and having a sequence identity to the polypeptide shown in SEQ ID NO: 38 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 38.

In some embodiments, the present invention relates to compositions comprising a carbohydrase, selected from cellulases, amylases, mannanases and xylanases, and a polypeptide obtainable from *Trichoderma reesei* and having a sequence identity to the polypeptide shown in SEQ ID NO: 39 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 39.

In some embodiments, the present invention relates to compositions comprising a carbohydrase, selected from cellulases, amylases, mannanases and xylanases, and a polypeptide obtainable from *Chaetomium thermophilum* and having a sequence identity to the polypeptide shown in SEQ ID NO: 40 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 40.

In some embodiments, the present invention relates to compositions comprising a carbohydrase, selected from cellulases, amylases, mannanases and xylanases, and a polypeptide obtainable from *Scytalidium thermophilum* and having a sequence identity to the polypeptide shown in SEQ ID NO: 41 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 41.

In some embodiments, the present invention relates to compositions comprising a carbohydrase, selected from cellulases, amylases, mannanases and xylanases, and a polypeptide obtainable from *Metapochonia suchlasporia* and having a sequence identity to the polypeptide shown in SEQ ID NO: 42 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 42.

In some embodiments, the present invention relates to compositions comprising a carbohydrase, selected from cellulases, amylases, mannanases and xylanases, and a polypeptide obtainable from *Daldinia fissa* and having a sequence identity to the polypeptide shown in SEQ ID NO: 43 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 43.

In some embodiments, the present invention relates to compositions comprising a carbohydrase, selected from cellulases, amylases, mannanases and xylanases, and a polypeptide obtainable from *Acremonium* sp. XZ2007 and having a sequence identity to the polypeptide shown in SEQ ID NO: 44 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 44.

In some embodiments, the present invention relates to compositions comprising a carbohydrase, selected from cellulases, amylases, mannanases and xylanases, and a polypeptide obtainable from *Acremonium dichromosporum* and having a sequence identity to the polypeptide shown in SEQ ID NO: 45 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 45.

In some embodiments, the present invention relates to compositions comprising a carbohydrase, selected from cellulases, amylases, mannanases and xylanases, and a polypeptide obtainable from *Sarocladium* sp. XZ2014 and having a sequence identity to the polypeptide shown in SEQ ID NO: 46 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 46.

In some embodiments, the present invention relates to compositions comprising a carbohydrase, selected from cellulases, amylases, mannanases and xylanases, and a polypeptide obtainable from *Metarhizium* sp. HNA15-2 and having a sequence identity to the polypeptide shown in SEQ ID NO: 47 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 47.

In some embodiments, the present invention relates to compositions comprising a carbohydrase, selected from cellulases, amylases, mannanases and xylanases, and a polypeptide obtainable from *Acremonium* sp. XZ2414 and having a sequence identity to the polypeptide shown in SEQ ID NO: 48 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 48.

In some embodiments, the present invention relates to compositions comprising a carbohydrase, selected from cellulases, amylases, mannanases and xylanases, and a polypeptide obtainable from *Isaria tenuipes* and having a sequence identity to the polypeptide shown in SEQ ID NO: 49 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 49.

In some embodiments, the present invention relates to compositions comprising a carbohydrase, selected from cellulases, amylases, mannanases and xylanases, and a polypeptide obtainable from *Scytalidium circinatum* and having a sequence identity to the polypeptide shown in SEQ ID NO: 50 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 50.

In some embodiments, the present invention relates to compositions comprising a carbohydrase, selected from cellulases, amylases, mannanases and xylanases, and a polypeptide obtainable from *Metarhizium lepidiotae* and having a sequence identity to the polypeptide shown in SEQ ID NO: 51 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 51.

In some embodiments, the present invention relates to compositions comprising a carbohydrase, selected from cellulases, amylases, mannanases and xylanases, and a polypeptide obtainable from *Thermobispora bispora* and having a sequence identity to the polypeptide shown in SEQ ID NO: 52 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 52.

In some embodiments, the present invention relates to compositions comprising a carbohydrase, selected from cellulases, amylases, mannanases and xylanases, and a polypeptide obtainable from *Sporormia fimetaria* and having a sequence identity to the polypeptide shown in SEQ ID NO: 53 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 53.

In some embodiments, the present invention relates to compositions comprising a carbohydrase, selected from cellulases, amylases, mannanases and xylanases, and a polypeptide obtainable from *Pycnidiophora* cf. *dispera* and having a sequence identity to the polypeptide shown in SEQ ID NO: 54 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 54.

In some embodiments, the present invention relates to compositions comprising a carbohydrase, selected from cellulases, amylases, mannanases and xylanases, and a polypeptide obtainable from Enviromental sample D and having a sequence identity to the polypeptide shown in SEQ ID NO: 55 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 55.

In some embodiments, the present invention relates to compositions comprising a carbohydrase, selected from cellulases, amylases, mannanases and xylanases, and a polypeptide obtainable from Enviromental sample O and having a sequence identity to the polypeptide shown in SEQ ID NO: 56 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 56.

In some embodiments, the present invention relates to compositions comprising a carbohydrase, selected from cellulases, amylases, mannanases and xylanases, and a polypeptide obtainable from Clavicipitaceae sp-70249 and having a sequence identity to the polypeptide shown in SEQ ID NO: 57 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 57.

In some embodiments, the present invention relates to compositions comprising a carbohydrase, selected from cellulases, amylases, mannanases and xylanases, and a polypeptide obtainable from *Westerdykella* sp. AS85-2 and having a sequence identity to the polypeptide shown in SEQ ID NO: 58 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 58.

In some embodiments, the present invention relates to compositions comprising a carbohydrase, selected from cellulases, amylases, mannanases and xylanases, and a polypeptide obtainable from *Humicolopsis cephalosporioides* and having a sequence identity to the polypeptide shown in SEQ ID NO: 59 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 59.

In some embodiments, the present invention relates to compositions comprising a carbohydrase, selected from cellulases, amylases, mannanases and xylanases, and a polypeptide obtainable from *Neosartorya massa* and having a sequence identity to the polypeptide shown in SEQ ID NO: 60 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 60.

In some embodiments, the present invention relates to compositions comprising a carbohydrase, selected from cellulases, amylases, mannanases and xylanases, and a polypeptide obtainable from *Roussoella intermedia* and having a sequence identity to the polypeptide shown in SEQ ID NO: 61 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 61.

In some embodiments, the present invention relates to compositions comprising a carbohydrase, selected from cellulases, amylases, mannanases and xylanases, and a polypeptide obtainable from *Pleosporales* and having a sequence identity to the polypeptide shown in SEQ ID NO: 62 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 62.

In some embodiments, the present invention relates to compositions comprising a carbohydrase, selected from cellulases, amylases, mannanases and xylanases, and a polypeptide obtainable from *Phaeosphaeria* and having a sequence identity to the polypeptide shown in SEQ ID NO: 63 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 63.

In some embodiments, the present invention relates to compositions comprising a carbohydrase, selected from cellulases, amylases, mannanases and xylanases, and a polypeptide obtainable from *Didymosphaeria futilis* and having a sequence identity to the polypeptide shown in SEQ ID NO: 64 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 64.

In some embodiments, the present invention relates to compositions comprising a carbohydrase, selected from cellulases, amylases, mannanases and xylanases, and a polypeptide obtainable from *Bacillus*, e.g., obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 65.

In some embodiments, the present invention relates to compositions comprising a carbohydrase, selected from cellulases, amylases, mannanases and xylanases, and a polypeptide obtainable from *Bacillus*, e.g., obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 66.

In some embodiments, the present invention relates to compositions comprising a carbohydrase, selected from cellulases, amylases, mannanases and xylanases, and a polypeptide obtainable from *Aspergillus*, e.g., obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 67.

In some embodiments, the present invention relates to compositions comprising a carbohydrase, selected from cellulases, amylases, mannanases and xylanases, and a polypeptide obtainable from *Trichoderma*, e.g., obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 68.

The DNases above may be combined with any of the carbohydrases below to form a blend to be added to a composition according to the invention.

Polypeptides Having Carbohydrase Activity (Carbohydrases)

Carbohydrase is a protein/enzyme that catalyse carbohydrates to break down carbohydrates to, e.g., simple sugar such as monosaccharides. Thus, carbohydrases are any of a group of enzymes that promote hydrolysis of a carbohydrate. Starch hydrolyzing carbohydrases (e.g., amylases) work on, e.g., amylose and amylopectin and non-starch carbohydrases includes enzymes which hydrolyze polymers made up of carbon sugars, e.g., cellulases which will ultimately produce glucose when complete hydrolysis is achieved. Another example is lactase which hydrolyses lactose to glucose and galactose. Examples of carbohydrases includes amylases, cellulases and mannanases. The carbohydrases to be incorporated in a composition according to the invention is preferably selected from xylanases, cellulases, mannanases and amylases.

Polypeptides Having Mannanase Activity

The term "mannanase" is defined here as an enzyme that hydrolyses compounds known as mannanes. The term "mannanase activity" is as an enzyme catalyzed hydrolysis of mannan, for purposes of the present invention, mannanase activity is determined according to the procedure described in the Assay II. Suitable mannanases include those of bacterial or fungal origin. Chemically or genetically modified mannanases are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. Commercially available mannanases are Mannaway (Novozymes A/S), and EFFECTENZ™ M1000 from Dupont. In one aspect, the present invention relates to a cleaning composition comprising at least one enzyme having mannanase activity, which may be obtained from a bacterial strain of the genus *Bacillus*. Preferably, a polypeptide selected from the group of polypeptides comprising the amino acid sequence shown in SEQ ID NO: 82. In one aspect the present invention relates to a cleaning composition comprising at least one enzyme classified in the EC 3.2.1.78 and which has mannanase activity.

Useful mannanases include polypeptides that are substantially homologous to the polypeptides shown in SEQ ID NO: 82 and species homologs (paralogs or orthologs) thereof.

The term "substantially homologous" is used herein to denote polypeptides having at least 60%, at least 65%, preferably at least 70%, more preferably at least 75%, more preferably at least 80%, more preferably at least 85%, more preferably at least 90% more preferably at least 95%, more preferably at least 97%, even more preferably at least 98% sequence identity to the sequence.

In some embodiments, the present invention relates compositions comprising a DNase and a polypeptide having a sequence identity to the polypeptide shown in SEQ ID NO: 82 of at least 60%, e.g., at least 65%, at least 70%, at least 75%, at least 80%, at least 85%, at least 90%, at least 95%, at least 96%, at least 97%, at least 98%, at least 99%, or 100% and which have mannanase activity. In one aspect, the polypeptides differ by up to 10 amino acids, e.g., 1, 2, 3, 4, 5, 6, 7, 8, 9, or 10, from the mature polypeptide shown in SEQ ID NO: 82.

The mannanase suitable for a composition of the invention may, in addition to the enzyme core comprising a catalytically domain, also comprise a cellulose binding domain (CBD), the cellulose binding domain and enzyme core (the catalytically active domain) of the enzyme being operably linked.

In one aspect, the present invention relates to a composition comprising a mannanase and a DNase, wherein the a mannanase is: i) polypeptide comprising an amino acid sequence as shown in SEQ ID NO:82; or ii) or a polypeptide having a sequence identity of at least 65%, at least 70%, at least 75%, at least 80%, at least 85%, at least 90%, at least 95%, at least 96%, at least 97%, at least 98%, or at least 99% to the amino acid sequence shown in SEQ ID NO: 82.

In one aspect, the present invention relates to a composition comprising a mannanase and a DNase, wherein the mannanase is selected from a polypeptide having at least 65%, at least 70%, at least 75%, at least 80%, at least 85%, at least 90%, at least 95%, at least 96%, at least 97%, at least 98%, or at least 99% or 100% sequence identity to the polypeptide shown in SEQ ID NO: 82.

Polypeptides Having Cellulase Activity

The term "cellulase" is defined in the present context as an enzyme that hydrolyses cellulose. In a preferred embodiment of the invention, the cellulase is an endoglucanase. The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate, as shown in Assay IV. Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0495257, EP 0531372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 02/99091 or a family 44 xyloglucanase, which a xyloglucanase enzyme having a sequence of at least 60% identity to positions 40-559 of SEQ ID NO: 2 of WO 01/62903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500 (B)™ (Kao Corporation), Revitalenz™ 1000, Revitalenz™ 2000, Revitalenz™ 3000 (Dupont).

In one aspect of the present invention, the cleaning composition comprise a DNase and a polypeptide having cellulase activity, which comprise the amino acid sequence of SEQ ID NO: 83. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 83.

In one aspect of the present invention, the cleaning composition comprise a DNase and a polypeptide having cellulase activity, which comprise the amino acid sequence of SEQ ID NO: 84. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 84.

In one aspect of the present invention, the cleaning composition comprise a DNase and a polypeptide having cellulase activity, which comprise the amino acid sequence of SEQ ID NO: 85. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 85.

In one aspect of the present invention, the cleaning composition comprise a DNase and a polypeptide having cellulase activity, which comprise the amino acid sequence of SEQ ID NO: 86. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 86.

In the present invention, the cleaning composition can also comprise a cellulase, which is a xyloglucanase. The term "xyloglucanase activity" is defined herein as an enzyme catalyzed hydrolysis of xyloglucan, which is shown in Assay III. Xyloglucanase can comprise parent xyloglucanase and the variants thereof.

In one embodiment of the present invention, the xyloglucanase is a polypeptide comprising an amino acid sequence of SEQ ID NO: 87. In one aspect of the present invention, the cleaning composition comprise a DNase and a polypeptide having xyloglucanase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 87.

Polypeptides Having Amylase Activity

An amylase is an enzyme that hydrolyses starch into sugars, for purposes of the present invention, amylase activity is determined according to the procedure described in the Assay V. Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

In one aspect of the present invention, the cleaning composition comprise a DNase and a polypeptide having amylase activity, which comprise the amino acid sequence of SEQ ID NO: 88. In one aspect of the present invention, the cleaning composition comprise a DNase and a polypeptide having amylase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, even most preferably at least 99% or 100% sequence identity to SEQ ID NO: 88.

In one aspect of the present invention, the cleaning composition comprise a DNase and a polypeptide having amylase activity, which comprise the amino acid sequence of SEQ ID NO: 89. In one aspect of the present invention, the cleaning composition comprise a DNase and a polypeptide having amylase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, even most preferably at least 99% or 100% sequence identity to SEQ ID NO: 89.

In one aspect of the present invention, the cleaning composition comprise a DNase and a polypeptide having amylase activity, which comprise the amino acid sequence of SEQ ID NO: 90. In one aspect of the present invention, the cleaning composition comprise a DNase and a polypeptide having amylase activity, which comprises an amino acid sequence at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, identity SEQ ID NO: 90.

In one aspect of the present invention, the cleaning composition comprise a DNase and a polypeptide having amylase activity, which comprise the amino acid sequence of SEQ ID NO: 91. In one aspect of the present invention, the cleaning composition comprise a DNase and a polypeptide having amylase activity, which comprises an amino acid sequence at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, identity SEQ ID NO: 91.

Additional amylases include amylases comprising the polypeptide shown in SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: 48, 49, 107, 156, 181, 190, 197, 201, 209 and 264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+Y305R+ G475K wherein the variants are C-terminally truncated and optionally further comprises a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K,
wherein the variants optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I
wherein the variants optionally further comprise a substitution at position 200 and/or a deletion at position 180 and/or position 181. Other suitable amylases are the alpha-amylase comprising the polypeptide sequence shown in SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Compositions

The invention relates to compositions, preferably cleaning compositions comprising a DNase and a carbohydrase in combination with one or more additional cleaning composition components.

One embodiment of the invention relates to a cleaning composition comprising a DNase, at least one carbohydrase and a cleaning component, wherein the carbohydrase is a cellulase, an amylase, a mannanase or a xylanase. The carbohydrase may be any of the cellulases, amylases, mannanases or xylanases mentioned under the heading "Polypeptides having cellulase, amylase, mannanase or xylanase activity" respectively.

As shown in the examples of the present invention carbohydrases such as cellulases act synergistically with the DNase in reduction, and removal of biofilm or components hereof. Biofilm is a complex structure comprising, the target substrate, e.g., the DNA may be embedded in the biofilm structure and It's believed that when the DNases and carbohydrases are acting together, the DNA components are more effectively dispersed or removed. It is thus advantageous to formulate DNases with carbohydrases such as cellulases, amylases, mannanases and xylanases in cleaning compositions, e.g., for deep cleaning. One aspect of the invention relates to a method of formulating a cleaning composition comprising adding a DNase, at least one carbohydrase and a cleaning component, wherein the carbohydrase is a cellulase, an amylase, a mannanase or a xylanase. The invention further relates to a kit intended for deep cleaning, wherein the kit comprises a solution of an enzyme mixture comprising a DNase and a carbohydrase, wherein the carbohydrase is a cellulase, an amylase, a mannanase or a xylanase.

In one aspect of the invention the carbohydrase is a cellulase. In one aspect, the invention relates to a cleaning composition comprising a DNase, a carbohydrase and a cleaning component, wherein the carbohydrase is a cellulase. In one aspect, the invention relates to a cleaning composition comprising a DNase, a carbohydrase and a cleaning component, wherein the carbohydrase is a cellulase, preferably selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

In one aspect of the invention the carbohydrase is an amylase.

In one aspect of the invention the carbohydrase is an amylase. In one aspect, the invention relates to a cleaning composition comprising a DNase, a carbohydrase and a cleaning component, wherein the carbohydrase is an amylase. In one aspect, the invention relates to a cleaning composition comprising a DNase, a carbohydrase and a cleaning component, wherein the carbohydrase is an amylase, preferably selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

In one aspect of the invention the carbohydrase is a mannanase. In one aspect, the invention relates to a cleaning composition comprising a DNase, a carbohydrase and a cleaning component, wherein the carbohydrase is a mannanase. In one aspect, the invention relates to a cleaning composition comprising a DNase, a carbohydrase and a cleaning component, wherein the carbohydrase is a mannanase, preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

In one aspect of the invention the carbohydrase is a xylanase. In one aspect, the invention relates to a cleaning composition comprising a DNase, a carbohydrase and a cleaning component, wherein the carbohydrase is a xylanase. In one aspect, the invention relates to a cleaning composition comprising a DNase, a carbohydrase and a cleaning component, wherein the carbohydrase is a xylanase, preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

The DNases to be formulated together with the carbohydrases or to be used together with the carbohydrases should be compatible with cleaning components. DNases are at present not standard ingredients in cleaning compositions. However, the applicant has identified DNases suitable for use in cleaning compositions, e.g., in WO 2017/060475, WO 2014/087011, WO 2015/155350 and WO 2015/155351. These applications also mentioned that DNases may be formulated with other enzymes, e.g., carbohydrases. However, none of these applications indicate that the DNases may have synergy with, e.g., cellulases. Enzymes, such as DNases should not only be compatible with the cleaning components, the DNases should also be compatible with other enzymes which may be present in a typical cleaning composition. Surprisingly, it was found that carbohydrases such as cellulases and DNases not only are compatible but even act synergistically in respect of biofilm reduction and removal, e.g., in deep cleaning.

Particularly useful DNases may be those of microbial origin. One embodiment of the invention relates to a cleaning composition comprising a DNase, a carbohydrase and at least one cleaning component, wherein the carbohydrase is a cellulase, an amylase, a mannanase or a xylanase and wherein the DNase is microbial, preferably obtained from bacteria or fungi. In one embodiment, the cleaning composition comprise a DNase from bacteria. One embodiment of the invention relates to a cleaning composition comprising a DNase, a carbohydrase and at least one cleaning component, wherein the carbohydrase is a cellulase, an amylase, a mannanase or a xylanase and wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

As mentioned above the DNases to be used in a composition of the invention preferable belong to the NUC1 group of DNases. The NUC1 group of DNases may comprise one or more of the motifs [T/D/S][G/N]PQL, [F/L/Y/I]A[N/R]D[L/I/P/V], or C[D/N]T[A/R]. One embodiment of the invention relates to a cleaning composition comprising a DNase, a carbohydrase, selected from cellulases, amylases, mannanases and xylanases, and at least one cleaning component, wherein the DNase comprises one or more of the motifs [T/D/S][G/N]PQL, [F/L/Y/I]A[N/R]D[L/I/P/V] or C[D/N]T[A/R]. The DNases preferably additionally comprises a NUC1_A domain [D/Q][I/V]DH.

One embodiment of the invention relates to a cleaning composition comprising a DNase, a carbohydrase, selected from cellulases, amylases, mannanases and xylanases, and at least one cleaning component, wherein the DNase comprises one or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises two or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises three or more motifs selected from the motifs [T/D/S][G/N]PQL, [F/L/Y/I]A[N/R]D[/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises four or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises all five motifs [T/D/S][G/N]PQL, [F/L/Y/I]A[N/R]D[U/I/P/V], C[D/N]T[A/R] and [D/Q][I/V]DH.

The DNases to be added to a composition of the invention preferably belong to the group of DNases comprised in the GYS-clade, which are NUC1 and NUC1_A DNases further comprising the conservative motifs [D/M/L][S/T]GYSR[D/N] (SEQ ID NO: 73) or ASXNRSKG (SEQ ID NO: 74) and which share similar structural and functional properties. The DNases of the GYS-clade are preferably obtained from *Bacillus* genus.

One embodiment of the invention relates to a cleaning composition comprising a DNase, at least one carbohydrase and a cleaning component, wherein the carbohydrase is a cellulase, an amylase, a mannanase or a xylanase and wherein the DNase comprises one or both of the motif(s) [D/M/L][S/T]GYSR[D/N] (SEQ ID NO: 73) or ASXNRSKG (SEQ ID NO: 74).

In a particularly preferred embodiment the *Bacillus* DNase comprises one or both of the motif(s) [D/M/L][S/T]GYSR[D/N] (SEQ ID NO: 73) or ASXNRSKG (SEQ ID NO: 74). In another particularly preferred embodiment the DNase comprises one or both of the motif(s) [D/M/L][S/T]GYSR[D/N] (SEQ ID NO: 73) or ASXNRSKG (SEQ ID NO: 74) and is obtained from *Bacillus cibi*. In yet another preferred embodiment the DNase comprises the amino acid sequence shown in SEQ ID NO: 13 or DNases closely related hereto.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

Other preferred DNases include those comprising the amino acid sequence shown in SEQ ID Nos: 65 and 66.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

The DNase may also preferably be fungal. Particularly preferred are DNases obtained from *Aspergillus* in particular, *Aspergillus oryzae*.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

Other particularly preferred are DNases obtained from *Trichoderma* in particular, *Trichoderma harzianum*.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment relates to a cleaning composition comprising a *Bacillus* DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment relates to a cleaning composition comprising a *Bacillus* DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment relates to a cleaning composition comprising a *Bacillus* DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment relates to a cleaning composition comprising a *Bacillus* DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment of the invention relates to a composition comprising
  a) at least 0.001 ppm, e.g., 0.1 ppm or 1 ppm of at least one polypeptide having DNase activity, wherein the DNase is selected for the group consisting of:
    i) a DNase comprising one or more of the motif(s) [T/D/S][G/N]PQL, [F/U/Y/I]A[N/R]D[L/I/P/V], C[D/N]T[A/R];
    ii) a DNase comprising the motif [D/Q][I/V]DH;
    iii) a DNase comprising one or both of the motif(s) [D/M/L][S/T]GYSR[D/N] (SEQ ID NO: 73) or ASXNRSKG (SEQ ID NO: 74);
    iv) a DNase comprising one or both of the motifs [V/I]PL[S/A]NAWK (SEQ ID NO: 75) or NPQL (SEQ ID NO: 76);
    v) a DNase comprising one or both of the motifs P[Q/E]L[W/Y] or [K/H/E]NAW;
    vi) a DNase selected from: a polypeptide having at least 80% sequence identity to the polypeptide shown in SEQ ID NO: 1, a polypeptide having at least 80% sequence identity to the polypeptide shown in SEQ ID NO: 2, a polypeptide having at least 80% sequence identity to the polypeptide shown in SEQ ID NO: 3, a polypeptide having at least 80% sequence identity to the polypeptide shown in SEQ ID NO: 4, a polypeptide having at least 80% sequence identity to the polypeptide shown in SEQ ID NO: 5, a polypeptide having at least 80% sequence identity to the polypeptide shown in SEQ ID NO: 6, a polypeptide having at least 80% sequence identity to the polypeptide shown in SEQ ID NO: 7, a polypeptide having at least 80% sequence identity to the polypeptide shown in SEQ ID NO: 8, a polypeptide having at least 80% sequence identity to the polypeptide shown in SEQ ID NO: 9, a polypeptide having at least 80% sequence identity to the polypeptide shown in SEQ ID NO: 10, a polypeptide having at least 80% sequence identity to the polypeptide shown in SEQ ID NO: 11, a polypeptide having at least 80% sequence identity to the polypeptide shown in SEQ ID NO: 12, a polypeptide having at least 80% sequence identity to the polypeptide shown in SEQ ID NO: 13, a polypeptide having at least 80% sequence identity to the polypeptide shown in SEQ ID NO: 14, a polypeptide having at least 80% sequence identity to the polypeptide shown in SEQ ID NO: 15, a polypeptide having at least 80% sequence identity to the polypeptide shown in SEQ ID NO: 16, a polypeptide having at least 80% sequence identity to the polypeptide shown in SEQ ID NO: 17, a polypeptide having at least 80% sequence identity to the polypeptide shown in SEQ ID NO: 18, a polypeptide having at least 80% sequence identity to the polypeptide shown in SEQ ID NO: 19, a polypeptide having at least 80% sequence identity to the polypeptide shown in SEQ ID NO: 20, a polypeptide having at least 80% sequence identity to the polypeptide shown in SEQ ID NO: 21, a polypeptide having at least 80% sequence identity to the polypeptide shown in SEQ ID NO: 22, a polypeptide having at least 80% sequence identity to the polypeptide shown in SEQ ID NO: 23, a polypeptide having at least 80% sequence identity to the polypeptide shown in SEQ ID NO: 24, a polypeptide having at least 80% sequence identity to the polypeptide shown in SEQ ID NO: 25, a polypeptide having at least 80% sequence identity to the polypeptide shown in SEQ ID NO: 26, a polypeptide having at least 80% sequence identity to the polypeptide shown in SEQ ID NO: 27, a polypeptide having at least 80% sequence identity to the polypeptide shown in SEQ ID NO: 28, a polypeptide having at least 80% sequence identity to the polypeptide shown in SEQ ID NO: 29, a polypeptide having at least 80% sequence identity to the polypeptide shown in SEQ ID NO: 30, a polypeptide having at least 80% sequence identity to the polypeptide shown in SEQ ID NO: 31, a polypeptide having at least 80% sequence identity to the polypeptide shown in SEQ ID NO: 32, a polypeptide having at least 80% sequence identity to the polypeptide shown in SEQ ID NO: 33, a polypeptide having at least 80% sequence identity to the polypeptide shown in SEQ ID NO: 34, a polypeptide having at least 80% sequence identity to the polypeptide shown in SEQ ID NO: 35, a polypeptide having at least 80% sequence identity to the polypeptide shown in SEQ ID NO: 36, a polypeptide having at least 80% sequence identity to the polypeptide shown in SEQ ID NO: 37, a polypeptide having at least 80% sequence identity to the polypeptide shown in SEQ ID NO: 38, a polypeptide having at least 80% sequence identity to the polypeptide shown in SEQ ID NO: 39, a polypeptide having at least 80% sequence identity to the polypeptide shown in SEQ ID NO: 40, a polypeptide having at least 80% sequence identity to the polypeptide shown in SEQ ID NO: 41, a polypeptide having at least 80% sequence identity to the polypeptide shown in SEQ ID NO: 42, a polypeptide having at least 80% sequence identity to the polypeptide shown in SEQ ID NO: 43, a polypeptide having at least 80% sequence identity to the polypeptide shown in SEQ ID NO: 44, a polypeptide having at least 80% sequence identity to the polypeptide shown in SEQ ID NO: 45, a polypeptide having at least 80% sequence identity to the polypeptide shown in SEQ ID NO: 46, a polypeptide having at least 80% sequence identity to the polypeptide shown in SEQ ID NO: 47, a polypeptide having at least 80% sequence identity to the polypeptide shown in SEQ ID NO: 48, a polypeptide having at least 80% sequence identity to the polypeptide shown in SEQ ID NO: 49, a polypeptide having at least 80% sequence identity to the polypeptide shown in SEQ ID NO: 50, a polypeptide having at least 80% sequence identity to the polypeptide shown in SEQ ID NO: 51, a polypeptide having at least 80% sequence identity to the polypeptide shown in SEQ ID NO: 52, a polypeptide having at least 80% sequence identity to the polypeptide shown in SEQ ID NO: 53, a polypeptide having at least 80% sequence identity to the polypeptide shown in SEQ ID NO: 54, a polypeptide having at least 80% sequence identity to the polypeptide shown in SEQ ID NO: 55, a polypeptide having at least 80% sequence identity to the polypeptide shown in SEQ ID NO: 56, a polypeptide having at least 80% sequence identity to the polypeptide shown in SEQ ID NO: 57, a polypeptide having at least 80% sequence identity to the polypeptide shown in SEQ ID NO: 58, a polypeptide having at least 80% sequence identity to the polypeptide shown in SEQ ID NO: 59, a polypeptide having at least 80% sequence identity to the polypeptide shown in SEQ ID NO: 60, a polypeptide having at least 80% sequence identity to the polypeptide shown in SEQ ID NO: 61, a polypeptide having at least 80% sequence identity to the polypeptide shown in SEQ ID NO: 62, a polypeptide having at least 80% sequence identity to the polypeptide shown in SEQ ID NO: 63, a polypeptide having at least 80% sequence identity to the polypeptide shown in SEQ ID NO: 64, a polypeptide having at least 80% sequence identity to the polypeptide shown in SEQ ID NO: 65, a polypeptide having at least 80% sequence identity to the polypeptide shown in SEQ ID NO: 66, a polypeptide having at least 80% sequence identity to the polypeptide shown in SEQ ID NO: 67, and a polypeptide having at least 80% sequence identity to the polypeptide shown in SEQ ID NO: 68; and b) at least 0.001 ppm, e.g., 0.1 ppm or 1 ppm of one or more carbohydrase, wherein the carbohydrase is selected from the group consisting of:
  i. a cellulase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 80% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86;
  ii. a xylanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87;
  iii. a mannanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82;
  iv. an amylase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91; and c) at least one additional component, e.g., cleaning component, preferably selected from surfactants, builders, bleach components, polymers and dispersing agents.

The carbohydrase and DNase may be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm. The DNases above may be combined with carbohydrases to form a blend to be added to the wash liquor solution according to the invention. The concentration of the DNase in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The concentration of the carbohydrases in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The DNases may be combined with any of the carbohydrases below to form a blend to be added to a composition according to the invention.

One embodiment relates to a cleaning composition comprising a DNase, a carbohydrase and at least one cleaning component, wherein the amount of DNase in the composition is from 0.01 to 1000 ppm and the amount of carbohydrase is from 0.01 to 1000 ppm.

The invention relates to cleaning compositions comprising an enzyme combination of the present invention in combination with one or more additional cleaning composition component(s). The choice of additional components is within the skill of the artisan and includes conventional ingredients, including the exemplary non-limiting components set forth below.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 0.1% to about 15%, such as about 1% to about 40%, or about 3% to about 20%, or about 3% to about 10%. The surfactant(s) is chosen based on the desired cleaning application, and may include any conventional surfactant(s) known in the art. When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. When included therein the detergent will usually contain from about 0.01% to about 10% by weight of a semipolar surfactant. Non-limiting examples of semipolar surfactants include amine oxides (AO) such as alkyldimethylamineoxide, N-(coco alkyl)-N, N-dimethylamine oxide and N-(tallow-alkyl)-N,N-bis(2-hydroxyethyl) amine oxide, and combinations thereof. When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50%, such as from about 0.5 to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1- ol), triethanolamine (TEA, also known as 2,2',2"-nitrilotriethan-1-ol), and (carboxymethyl) inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N, N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N, N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N, N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The detergent may contain 0-30% by weight, such as about 1% to about 20%, such as from about 0.01 to about 10 wt. % of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn (O)3Mn(Me3-TACN)](PF6) 2, and [2,2',2"-nitrilotris(ethane-1,2-diylazanylylidene-κN-methanylylidene)triphenolato-κ3O]manganese (III). The bleach catalysts may also be other metal compounds; such as iron or cobalt complexes.

In some embodiments, where a source of a peracid is included, an organic bleach catalyst or bleach booster may be used having one of the following formulae:

(i)

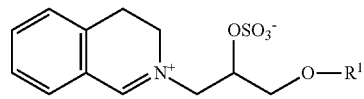

(ii)

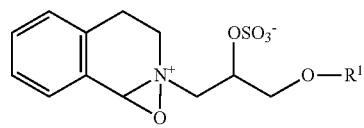

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate.

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl) cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt. % to 0.2 wt. % fabric hueing agent, this may be especially preferred when the composition is in the form of a unit dose pouch. Suitable hueing agents are also disclosed in, e.g., WO 2007/087257 and WO 2007/087243.

Enzymes

The detergent additive as well as the detergent composition may comprise one or more additional enzymes such as one or more protease, lipase, cutinase, pectinase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

The term "protease activity" means a proteolytic activity (EC 3.4). Proteases usably in cleaning compositions of the present invention are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

The most widely used proteases in the detergent industry such as laundry and dish wash are the serine proteases. Serine proteases is a subgroup of proteases characterised by having a serine in the active site, which forms a covalent adduct with the substrate. Serine proteases are characterized by having two active site amino acid residues apart from the serine, namely a histidine residue and an aspartic acid residue. Subtilase refer to a sub-group of serine protease according to Siezen et al., 1991, *Protein Engng.* 4:719-737 and Siezen et al., 1997, *Protein Science* 6:501-523. The subtilases may be divided into 6 sub-divisions, i.e., the Subtilisin family, the Thermitase family, the Proteinase K family, the Lantibiotic peptidase family, the Kexin family and the Pyrolysin family.

Suitable proteases for the compositions of the invention include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO 2009/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/26024 and WO 02/16547. Examples of trypsin-like proteases are trypsin (e.g., of porcine or bovine origin) and the *Fusarium* protease described in WO 89/06270, WO 94/25583 and WO 2005/040372, and the chymotrypsin proteases derived from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloproteases as described in WO 2007/044993 (Genencor Int.) such as those derived from *Bacillus amyloliquefaciens*.

Examples of useful proteases are the variants described in: WO 92/19729, WO 96/034946, WO 98/20115, WO 98/20116, WO 99/11768, WO 01/44452, WO 03/006602, WO 2004/03186, WO 2004/041979, WO 2007/006305, WO 2011/036263, WO 2011/036264, especially protease variants comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the *Bacillus lentus* protease shown in SEQ ID NO: 79. More preferred the protease variants may comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO: 79 or the *Bacillus amyloliquefaciens* protease (BPN') shown in SEQ ID NO: 80. The protease variants preferably have at least 80% sequence identity to SEQ ID NO: 79 or SEQ ID NO: 80.

A protease variant comprising a substitution at one or more positions corresponding to positions 171, 173, 175, 179, or 180 of SEQ ID NO: 81, wherein said protease variant has a sequence identity of at least 75% but less than 100% to SEQ ID NO: 81.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxPR, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl) stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil Release Polymers

The cleaning compositions of the present invention may also include one or more soil release polymers which aid the removal of soils from fabrics such as cotton and polyester based fabrics, in particular, the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt. % zeolite (anhydrous basis); and (c) less than 10 wt. % phosphate salt (anhydrous basis), wherein said enzyme co-granule comprises from 10 to 98 wt. % moisture sink component and the composition additionally comprises from 20 to 80 wt. % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase and at least one carbohydrase and a cleaning component, wherein the carbohydrase is a cellulase, an amylase, a mannanase or a xylanase. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 µm, particularly 50-1500 µm, 100-1500 µm or 250-1200 µm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. In a one embodiment, the thickness of the coating is below 100 µm. In another embodiment, the thickness of the coating is below 60 µm. In an even more particular embodiment the total thickness of the coating is below 40 µm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, and may have a solubility of at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4$:$7H_2O$), zinc sulfate heptahydrate ($ZnSO_4$:$7H_2O$), sodium phosphate dibasic heptahydrate ($Na_2HPO_4$$7H_2O$), magnesium nitrate hexahydrate ($Mg(NO_3)_2(6H_2O)$), sodium citrate dihydrate and magnesium acetate tetrahydrate. Preferably, the salt is applied as a solution of the salt, e.g., using a fluid bed.

One embodiment of the present invention provides a granule, which comprises:
(a) a core comprising a DNase and a carbohydrase, wherein the carbohydrase is a cellulase, an amylase, a mannanase or a xylanase, and
(b) optionally a coating consisting of one or more layer(s) surrounding the core.

One embodiment of the invention relates to a granule, which comprises:
(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, and
(b) optionally a coating consisting of one or more layer(s) surrounding the core.

One embodiment of the invention relates to a granule, which comprises:
(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, and
(b) optionally a coating consisting of one or more layer(s) surrounding the core.

One embodiment of the invention relates to a granule, which comprises:
(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, and
(b) optionally a coating consisting of one or more layer(s) surrounding the core.

One embodiment of the invention relates to a granule, which comprises:
(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, and
(b) optionally a coating consisting of one or more layer(s) surrounding the core.

One embodiment of the invention relates to a granule, which comprises:
(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65, and (b) optionally a coating consisting of one or more layer(s) surrounding the core.

One embodiment of the invention relates to a granule, which comprises:
(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65, and
(b) optionally a coating consisting of one or more layer(s) surrounding the core.

One embodiment of the invention relates to a granule, which comprises:
(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65, and
(b) optionally a coating consisting of one or more layer(s) surrounding the core.

One embodiment of the invention relates to a granule, which comprises:
(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 65, and
(b) optionally a coating consisting of one or more layer(s) surrounding the core.

One embodiment of the invention relates to a granule, which comprises:
(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66, and
(b) optionally a coating consisting of one or more layer(s) surrounding the core.

One embodiment of the invention relates to a granule, which comprises:
(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66, and
(b) optionally a coating consisting of one or more layer(s) surrounding the core.

One embodiment of the invention relates to a granule, which comprises:
(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66, and
(b) optionally a coating consisting of one or more layer(s) surrounding the core.

One embodiment of the invention relates to a granule, which comprises:
(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 66, and (b) optionally a coating consisting of one or more layer(s) surrounding the core.

One embodiment of the invention relates to a granule, which comprises:
(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67, and (b) optionally a coating consisting of one or more layer(s) surrounding the core.

One embodiment of the invention relates to a granule, which comprises:
(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67, and (b) optionally a coating consisting of one or more layer(s) surrounding the core.

One embodiment of the invention relates to a granule, which comprises:
(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67, and (b) optionally a coating consisting of one or more layer(s) surrounding the core.

One embodiment of the invention relates to a granule, which comprises:
(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 67, and (b) optionally a coating consisting of one or more layer(s) surrounding the core.

One embodiment of the invention relates to a granule, which comprises:
(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68, and (b) optionally a coating consisting of one or more layer(s) surrounding the core.

One embodiment of the invention relates to a granule, which comprises:
(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 68, and (b) optionally a coating consisting of one or more layer(s) surrounding the core.

Uses

The present invention is also directed to methods for using the compositions thereof. Laundry/textile/fabric (House hold laundry washing, Industrial laundry washing). Hard surface cleaning (ADW, car wash, Industrial surface). The compositions of the invention comprise a blend of DNase and carbohydrase, selected from a cellulase, an amylase, a mannanase or a xylanase and effectively reduce or remove organic components, such as protein and DNA from surfaces such as textiles and hard surfaces, e.g., dishes.

The compositions of the invention comprise a blend of DNase and carbohydrase, wherein the carbohydrase is a cellulase, an amylase, a mannanase or a xylanase, and effectively reduce or remove organic components, such as mannan, starch, cellulose, xyloglucan and DNA from surfaces such as textiles and hard surfaces, e.g., dishes. One embodiment of the invention relates to the use of a cleaning composition comprising a DNase, a carbohydrase, selected from a cellulase, an amylase, a mannanase or a xylanase and at least one cleaning component for reduction or removal of components of biofilm, such as DNA and at least one carbohydrase and a cleaning component, wherein the carbohydrase is a cellulase, an amylase, a mannanase or a xylanase, of an item, wherein the item is a textile or a hard surface.

One embodiment of the invention relates to the use of a cleaning composition comprising a DNase, at least one carbohydrase and a cleaning component, wherein the carbohydrase is a cellulase, an amylase, a mannanase or a xylanase for deep cleaning of an item, wherein the item is a textile or a surface.

One embodiment of the invention relates to the use of a composition comprising a DNase and a carbohydrase, wherein the carbohydrase is a cellulase, an amylase, a mannanase or a xylanase for reduction or removal of biofilm and/or compounds such as mannan, starch, cellulose, xyloglucan and DNA of an item. One embodiment of the invention relates to the use of a cleaning composition comprising a DNase and a carbohydrase, wherein the carbohydrase is a cellulase, an amylase, a mannanase or a xylanase for reduction or removal of biofilm and/or compounds such as mannan, starch, cellulose, xyloglucan and DNA of an item such as textile. One embodiment of the invention relates to the use of a cleaning composition comprising a DNase and a carbohydrase, wherein the carbohydrase is a cellulase, an amylase, a mannanase or a xylanase for deep cleaning when the cleaning composition is applied in, e.g., laundry process.

One embodiment of the invention relates to the use of a composition comprising a DNase and carbohydrase, selected from a cellulase, an amylase, a mannanase or a xylanase for reduction of redeposition or reduction of malodor. One embodiment of the invention relates to the use of a cleaning composition comprising a DNase and carbohydrase, selected from a cellulase, an amylase, a mannanase or a xylanase for reduction of redeposition or reduction of malodor.

One embodiment of the invention relates to the use of a cleaning composition comprising a DNase and carbohydrase, selected from a cellulase, an amylase, a mannanase or a xylanase for reduction of redeposition or reduction of malodor when the cleaning composition is applied in, e.g., laundry process. One embodiment of the invention relates to the use of a cleaning composition comprising a DNase and carbohydrase, selected from a cellulase, an amylase, a mannanase or a xylanase for reduction of redeposition or reduction of malodor on an item, e.g., textile. In one embodiment, the composition is an anti-redeposition composition.

One embodiment of the invention relates to the use of a cleaning composition comprising a DNase and a cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment of the invention relates to the use of a cleaning composition comprising a DNase and an amylase for deep cleaning of an item or reduction of redeposition or malodor, wherein the amylase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment of the invention relates to the use of a cleaning composition comprising a DNase and a mannanase for deep cleaning of an item or reduction of redeposition or malodor, wherein the mannanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to the use of a cleaning composition comprising a DNase and a xylanase for deep cleaning of an item or reduction of redeposition or malodor, wherein the xylanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 65.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 66.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 67.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO: 68.

The invention further relates to a method of deep cleaning of an item, wherein the item may be textile or hard surface preferably is a textile.

One embodiment of the invention relates to a method of deep cleaning on an item, comprising the steps of:
  a) contacting the item with a cleaning composition according to the invention; and
  b) optionally rinsing the item, wherein the item is preferably a textile.

One embodiment of the invention relates to a method of deep cleaning on an item, comprising the steps of:
  a) contacting the item with a solution comprising an enzyme mixture comprising a DNase, a carbohydrase, wherein the carbohydrase is a cellulase, an amylase, a mannanase or a xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
  b) optionally rinsing the item, wherein the item is preferably a textile.

One embodiment of the invention relates to a method of deep cleaning on an item, comprising the steps of:
  a) contacting the item with a solution comprising an enzyme mixture comprising a DNase, a cellulase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment of the invention relates to a method of deep cleaning on an item, comprising the steps of:

a) contacting the item with a solution comprising an enzyme mixture comprising a DNase, an amylase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment of the invention relates to a method of deep cleaning on an item, comprising the steps of:

a) contacting the item with a solution comprising an enzyme mixture comprising a DNase, mannanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to a method of deep cleaning on an item, comprising the steps of:

a) contacting the item with a solution comprising an enzyme mixture comprising a DNase, xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

One embodiment of the invention relates to a method of deep cleaning on an item, comprising the steps of:

a) contacting the item with a solution comprising an enzyme mixture comprising a DNase, a cellulase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, SEQ ID NO: 65, SEQ ID NO: 66, SEQ ID NO: 67 or SEQ ID NO: 68.

One embodiment of the invention relates to a method of deep cleaning on an item, comprising the steps of:

a) contacting the item with a solution comprising an enzyme mixture comprising a DNase, an amylase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, SEQ ID NO: 65, SEQ ID NO: 66, SEQ ID NO: 67 or SEQ ID NO: 68.

One embodiment of the invention relates to a method of deep cleaning on an item, comprising the steps of:
 a) contacting the item with a solution comprising an enzyme mixture comprising a DNase, mannanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
 b) optionally rinsing the item, wherein the item is preferably a textile;
wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, SEQ ID NO: 65, SEQ ID NO: 66, SEQ ID NO: 67 or SEQ ID NO: 68.

One embodiment of the invention relates to a method of deep cleaning on an item, comprising the steps of:
 a) contacting the item with a solution comprising an enzyme mixture comprising a DNase, xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
 b) optionally rinsing the item, wherein the item is preferably a textile;
wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO: 13, SEQ ID NO: 65, SEQ ID NO: 66, SEQ ID NO: 67 or SEQ ID NO: 68.

The invention is further described in the following paragraphs

Paragraph 1. A cleaning composition comprising at least 0.001 ppm DNase and at least 0.001 ppm carbohydrase and a cleaning component, wherein the cleaning component is selected from
 a. 0.1 to 15 wt. % of at least one a surfactant;
 b. 0.5 to 20 wt. % of at least one builder; and
 c. 0.01 to 10 wt. % of at least one bleach component.

Paragraph 2. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a cellulase.

Paragraph 3. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a mannanase.

Paragraph 4. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a amylase.

Paragraph 5. The cleaning composition according to any of paragraphs 1 to 4, wherein the DNase is selected from the group of polypeptides:
 a) a polypeptide having at least 80% sequence identity to the polypeptide shown in SEQ ID NO: 1,
 b) a polypeptide having at least 80% sequence identity to the polypeptide shown in SEQ ID NO: 2,
 c) a polypeptide having at least 80% sequence identity to the polypeptide shown in SEQ ID NO: 3,
 d) a polypeptide having at least 80% sequence identity to the polypeptide shown in SEQ ID NO: 4,
 e) a polypeptide having at least 80% sequence identity to the polypeptide shown in SEQ ID NO: 5,
 f) a polypeptide having at least 80% sequence identity to the polypeptide shown in SEQ ID NO: 6,
 g) a polypeptide having at least 80% sequence identity to the polypeptide shown in SEQ ID NO: 7,
 h) a polypeptide having at least 80% sequence identity to the polypeptide shown in SEQ ID NO: 8,
 i) a polypeptide having at least 80% sequence identity to the polypeptide shown in SEQ ID NO: 9,
 j) a polypeptide having at least 80% sequence identity to the polypeptide shown in SEQ ID NO: 10,
 k) a polypeptide having at least 80% sequence identity to the polypeptide shown in SEQ ID NO: 11,
 l) a polypeptide having at least 80% sequence identity to the polypeptide shown in SEQ ID NO: 12,
 m) a polypeptide having at least 80% sequence identity to the polypeptide shown in SEQ ID NO: 13,
 n) a polypeptide having at least 80% sequence identity to the polypeptide shown in SEQ ID NO: 14,
 o) a polypeptide having at least 80% sequence identity to the polypeptide shown in SEQ ID NO: 15,
 p) a polypeptide having at least 80% sequence identity to the polypeptide shown in SEQ ID NO: 16,
 q) a polypeptide having at least 80% sequence identity to the polypeptide shown in SEQ ID NO: 17,
 r) a polypeptide having at least 80% sequence identity to the polypeptide shown in SEQ ID NO: 18,
 s) a polypeptide having at least 80% sequence identity to the polypeptide shown in SEQ ID NO: 19,
 t) a polypeptide having at least 80% sequence identity to the polypeptide shown in SEQ ID NO: 20,
 u) a polypeptide having at least 80% sequence identity to the polypeptide shown in SEQ ID NO: 21,
 v) a polypeptide having at least 80% sequence identity to the polypeptide shown in SEQ ID NO: 22,
 w) a polypeptide having at least 80% sequence identity to the polypeptide shown in SEQ ID NO: 23,
 x) a polypeptide having at least 80% sequence identity to the polypeptide shown in SEQ ID NO: 24, and
 y) a polypeptide having at least 80% sequence identity to the polypeptide shown in SEQ ID NO: 25, and
wherein the carbohydrase is selected from the group consisting of:
 i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;

ii. a xylanase selected from a polypeptide having at least 80% sequence identity to the polypeptide shown in SEQ ID NO: 87;

iii. a mannanase selected from a polypeptide having at least 80% sequence identity to the polypeptide shown in SEQ ID NO: 82; and iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 6. The cleaning composition according to paragraph 1, wherein the DNase comprises one or both of the motifs [V/I]PL[S/A]NAWK (SEQ ID NO: 75) or NPQL (SEQ ID NO: 76) and the carbohydrase is a cellulase.

Paragraph 7. The cleaning composition according to paragraph 1, wherein the DNase comprises one or both of the motifs [V/I]PL[S/A]NAWK (SEQ ID NO: 75) or NPQL (SEQ ID NO: 76) and the carbohydrase is a mannanase.

Paragraph 8. The cleaning composition according to paragraph 1, wherein the DNase comprise one or both of the motifs [V/I]PL[S/A]NAWK (SEQ ID NO: 75) or NPQL (SEQ ID NO: 76) and the carbohydrase is a amylase.

Paragraph 9. The cleaning composition according to any of paragraphs 1 and 6 to 8, wherein the DNase is selected from the group of polypeptides:
  a) a polypeptide having at least 80% sequence identity to the polypeptide shown in SEQ ID NO: 26,
  b) a polypeptide having at least 80% sequence identity to the polypeptide shown in SEQ ID NO: 27,
  c) a polypeptide having at least 80% sequence identity to the polypeptide shown in SEQ ID NO: 28,
  d) a polypeptide having at least 80% sequence identity to the polypeptide shown in SEQ ID NO: 29,
  e) a polypeptide having at least 80% sequence identity to the polypeptide shown in SEQ ID NO: 30,
  f) a polypeptide having at least 80% sequence identity to the polypeptide shown in SEQ ID NO: 31,
  g) a polypeptide having at least 80% sequence identity to the polypeptide shown in SEQ ID NO: 32,
  h) a polypeptide having at least 80% sequence identity to the polypeptide shown in SEQ ID NO: 33,
  i) a polypeptide having at least 80% sequence identity to the polypeptide shown in SEQ ID NO: 34,
  j) a polypeptide having at least 80% sequence identity to the polypeptide shown in SEQ ID NO: 35,
  k) a polypeptide having at least 80% sequence identity to the polypeptide shown in SEQ ID NO: 36,
  l) a polypeptide having at least 80% sequence identity to the polypeptide shown in SEQ ID NO: 37,
  m) a polypeptide having at least 80% sequence identity to the polypeptide shown in SEQ ID NO: 38, and
wherein the carbohydrase is selected from the group consisting of:
  i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;

ii a xylanase selected from a polypeptide having at least 80% sequence identity to the polypeptide shown in SEQ ID NO: 87;

iii. a mannanase selected from a polypeptide having at least 80% sequence identity to the polypeptide shown in SEQ ID NO: 82; and iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 10. The cleaning composition according to paragraph 1, wherein the DNase comprises one or both of the motifs P [Q/E]L[W/Y] or [K/H/E]NAW and the carbohydrase is a cellulase.

Paragraph 11. The cleaning composition according to paragraph 1, wherein the DNase comprise one or both of the motifs P [Q/E]L[W/Y] or [K/H/E]NAW and the carbohydrase is a mannanase.

Paragraph 12. The cleaning composition according to paragraph 1, wherein the DNase comprise one or both of the motifs P [Q/E]L[W/Y] or [K/H/E]NAW and the carbohydrase is an amylase.

Paragraph 13. The cleaning composition according to paragraph 1 or 10 to 12, wherein the DNase is selected from the group of polypeptides:
  a) a polypeptide having at least 80% sequence identity to the polypeptide shown in SEQ ID NO: 39,
  b) a polypeptide having at least 80% sequence identity to the polypeptide shown in SEQ ID NO: 40,
  c) a polypeptide having at least 80% sequence identity to the polypeptide shown in SEQ ID NO: 41,
  d) a polypeptide having at least 80% sequence identity to the polypeptide shown in SEQ ID NO: 42,
  e) a polypeptide having at least 80% sequence identity to the polypeptide shown in SEQ ID NO: 43
  f) a polypeptide having at least 80% sequence identity to the polypeptide shown in SEQ ID NO: 44,
  g) a polypeptide having at least 80% sequence identity to the polypeptide shown in SEQ ID NO: 45,
  h) a polypeptide having at least 80% sequence identity to the polypeptide shown in SEQ ID NO: 46,
  i) a polypeptide having at least 80% sequence identity to the polypeptide shown in SEQ ID NO: 47,
  j) a polypeptide having at least 80% sequence identity to the polypeptide shown in SEQ ID NO: 48,
  k) a polypeptide having at least 80% sequence identity to the polypeptide shown in SEQ ID NO: 49,
  l) a polypeptide having at least 80% sequence identity to the polypeptide shown in SEQ ID NO: 50,
  m) a polypeptide having at least 80% sequence identity to the polypeptide shown in SEQ ID NO: 51, and
wherein the carbohydrase is selected from the group consisting of;
  i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;

ii a xylanase selected from a polypeptide having at least 80% sequence identity to the polypeptide shown in SEQ ID NO: 87;
iii. a mannanase selected from a polypeptide having at least 80% sequence identity to the polypeptide shown in SEQ ID NO: 82; and
iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 14. The cleaning composition according to paragraph 1, wherein the DNase is selected from the group consisting of:
a) polypeptide obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
b) polypeptide obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
c) polypeptide obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
d) polypeptide obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity, and
wherein the carbohydrase is selected from the group consisting of:
i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;
ii. a xylanase selected from a polypeptide having at least 80% sequence identity to the polypeptide shown in SEQ ID NO: 87;
ii. a mannanase selected from a polypeptide having at least 80% sequence identity to the polypeptide shown in SEQ ID NO: 82; and
iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 15. The use of a composition according to any of the previous paragraphs for deep cleaning of an item, wherein the item is a textile or a surface.

Paragraph 16. A method of formulating a cleaning composition comprising adding a DNase, a carbohydrase and at least one cleaning component.

Paragraph 17. A kit intended for deep cleaning, wherein the kit comprises a solution of an enzyme mixture comprising a DNase, carbohydrase and optionally a protease.

Paragraph 18. A method of deep cleaning on an item, comprising the steps of:
a) contacting the item with a solution comprising an enzyme mixture comprising a DNase and a carbohydrase and optionally a protease; and a cleaning component, wherein the cleaning component is selected from 0.1 to 15 wt. % of at least one a surfactant; 0.5 to 20 wt. % of at least one builder; and 0.01 to 10 wt. % of at least one bleach component; and
b) optionally rinsing the item, wherein the item is preferably a textile.

Definitions

Biofilm is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. In one aspect, the biofilm producing strain is *Brevundimonas* sp. In one aspect, the biofilm producing strain is *Pseudomonas alcaliphila* or *Pseudomonas fluorescens*. In one aspect, the biofilm producing strain is *Staphylococcus aureus*.

By the term "deep cleaning" is meant reduction, disruption or removal of components of organic matter, e.g., biofilm, such as polysaccharides, proteins, DNA, soil or other components present in the organic matter.

Cleaning component: The cleaning component, e.g., the detergent adjunct ingredient is different to the DNase and carbohydrase. The precise nature of these additional cleaning components, e.g., adjunct components, and levels of incorporation thereof, will depend on the physical form of the composition and the nature of the operation for which it is to be used. Suitable cleaning components, e.g., adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term "cleaning composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme blend of the invention, the detergent formulation may contain one or more additional enzymes (such as proteases, lipases, cutinases, endoglucanases, xyloglucanases, pectinases, pectin lyases, xanthanases, peroxidases, haloperoxygenases and catalases or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides. Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during, e.g., wash or hard surface cleaning.

The term "whiteness" is defined herein as a greying, yellowing of a textile. Loss of whiteness may be due to removal of optical brighteners/hueing agents. Greying and yellowing can be due to soil redeposition, body soils, coloring from, e.g., iron and copper ions or dye transfer. Whiteness might include one or several issues from the list below: colourant or dye effects; incomplete stain removal (e.g., body soils, sebum etc.); redeposition (greying, yellowing or other discolourations of the object) (removed soils reassociate with other parts of textile, soiled or unsoiled); chemical changes in textile during application; and clarification or brightening of colors.

The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g., polyamide fiber, acrylic fiber, polyester fiber, polyvinyl chloride fiber, polyurethane fiber, polyurea fiber, aramid fiber), and/or cellulose-containing fiber (e.g., rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

EXAMPLES

Assays
Assay I: Testing of DNase Activity

DNase activity was determined on DNase Test Agar with Methyl Green (BD, Franklin Lakes, NJ, USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petri dishes with and allowed to solidify by incubation o/n at room temperature. On solidified agar plates, 5 µl of enzyme solutions are added and DNase activity is observed as colorless zones around the spotted enzyme solutions.

Assay II: Testing of Mannanase Activity

Mannanase activity may be tested according to standard test procedures known in the art, such as by applying a solution to be tested to 4 mm diameter holes punched out in agar plates containing 0.2% AZCL galactomannan (carob), i.e., substrate for the assay of endo-1,4-beta-D-mannanase available as CatNo.I-AZGMA from the company Megazyme (Megazyme's Internet address: megazyme.com/Purchase/index.html).

Assay III: Testing of Xyloglucanase Activity

The reaction involves endo hydrolysis of 1,4-beta-D-glucosidic linkages in xyloglucan. For purposes of the present invention, xyloglucanase activity is determined using AZCL-xyloglucan (from Megazyme) as the reaction substrate. The assay can be performed in several ways, e.g., as described in Example 2 of the present application or as described in WO 01/62903. One unit of xyloglucanase activity (XyloU) is defined by reference to the assay method described in WO 01/62903, page 60, lines 3-17.

Assay IV: Testing of Cellulase Activity

The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate.

Example 1

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C. Laundry was sampled immediately after washing at 15, 40 and 60° C., respectively. Twenty grams of laundry was added 0.9% (w/v) NaCl (1.06404; Merck, Darmstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at –80° C. in TSB containing 20% (w/v) glycerol (49779; Sigma).

Preparation of Swatches with Biofilm

Swatches with biofilm of *Brevundimonas* sp. was included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD600 nm of 0.03, and 50 mL was added into a petri dish (diameter 125 mm), in which a swatch (80 mm×120 mm) of sterile cotton (WFK10A). After incubation (48 hours at 15° C. with shaking (100 rpm), swatches were rinsed twice with 0.9% (w/v) NaCl and dried in LAF bench for 60 min. Swatches were stored at 4° C. prior to wash.

Example 2

Wash Experiment

Wash experiment was performed using the Automatic Mechanical Stress Assay (AMSA). With AMSA, the wash performance of many small volume enzyme-detergent solutions can be examined at the same time. The AMSA plate has many slots for test solutions, and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner.

The wash experiment was conducted under the experimental conditions specified below:

| Detergent dosage | 3.3 g/L (liquid detergent) |
|---|---|
| Test solution volume | 160 micro L |
| pH | pH 8 |
| Wash time | 20 minutes |
| Temperature | 30° C. |
| Water hardness | 15° dH |
| Soil | Wfk09V 0.7 g/L |

Model detergents and test materials were as follows:

| Laundry liquid model detergent | Model detergent A |
|---|---|
| Test material | *Brevundimonas* sp. 2-day biofilm grown on WFK10 (cotton) or WFK30A (polyester) |

For wash experiments, Model detergent A (containing 12% LAS, 11% AEO Biosoft N25-7 (NI), 7% AEOS (SLES), 6% MPG, 3% ethanol, 3% TEA, 2.75% cocoa soap, 2.75% soya soap, 2% glycerol, 2% sodium hydroxide, 2% sodium citrate, 1% sodium formate, 0.2% DTMPA and 0.2% PCA (all percentages are w/w)) (3.3 g/L) dissolved in water hardness 15° dH (Ca:Mg:NaHCO3-=4:1:1.5) was used. Soil was subsequently added to reach a concentration of 0.7 g soil/L (WFK09V pigment soil) to reveal biofilm. After washing, textiles were flushed in tap water and dried over night before scanning. Wash experiments were done twice.

Wash performance was measured as the brightness of the WFK09V pigment soiled, washed textile. Brightness can also be expressed as the intensity of the light reflected from the sample when illuminated with white light. When the sample is soiled, the intensity of the reflected light is lower, than that of a clean sample. Therefore, the intensity of the reflected light can be used to measure wash performance. Intensity measurements were made with a professional flatbed scanner (Kodak iQsmart, Kodak, Midtager 29, DK-2605 Brøndby, Denmark), which was used to capture an image of the washed and dried textile. To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}$$

Example 3: Wash Synergy Between DNase and Cellulase

To assess wash synergy between DNase (SEQ ID NO: 13) and cellulase (SEQ ID NO: 85) biofilm-harboring textile was AMSA washed a) in the absence of enzyme (blank), b) in the presence of DNase alone, c) in the presence of cellulase alone and d) with a mixture of DNase and cellulase. The resulting textile intensities and corresponding wash performances (WPs) are listed in Tables 1 and 2. Wash performances attributable to DNase ($WP_{DNase}$), cellulase ($WP_{Cellu}$) and the mixture of the two ($WP_{DNase+Cellu}$) were quantified as the difference in intensity between textile washed with and without enzyme: $WP_{DNase} = I_{DNase} - I_{Blank}$, $WP_{Cellu} = I_{Cellu} - I_{Blank}$, $WP_{DNase+Cellu} = I_{DNase+Cellu} - I_{Blank}$. The synergistic component of wash performance $WP_{syn}$ was quantified as the extent to which wash performance of mixed DNase and cellulase ($WP_{DNase+Cellu}$) exceeded the sum of the individual wash performances of DNase alone and cellulase alone: $WP_{syn} = WP_{DNase+Cellu} - (WP_{DNase} + WP_{Cellu})$.

TABLE 1 synergistic wash effect of DNase and cellulase (wash experiment 1)

| | Cellulase (SEQ ID NO: 85) | I | WP | $WP_{syn}$ |
|---|---|---|---|---|
| Blank | No enzyme | 285.460 | — | — |
| DNase | 0.00002 ppm DNase | 298.681 | 13.22 | — |
| Cellulase | 0.015% Cellulase | 289.347 | 3.89 | — |
| | 0.15% Cellulase | 290.955 | 5.49 | — |
| DNase + Cellulase | 0.00002 ppm DNase + 0.015% Cellulase | 304.770 | 19.31 | 2.20 |
| | 0.00002 ppm DNase + 0.15% Cellulase | 310.821 | 25.36 | 6.65 |

TABLE 2 synergistic wash effect of DNase and cellulase (wash experiment 2)

| | Cellulose (SEQ ID NO: 91) | I | WP | $WP_{syn}$ |
|---|---|---|---|---|
| Blank | No enzyme | 286.616 | — | — |
| DNase | 0.00002 ppm DNase | 322.453 | 35.84 | — |
| Cellulase | 0.015% Cellulase | 287.859 | 1.24 | — |
| | 0.15% Cellulase | 291.329 | 4.71 | — |
| DNase + Cellulase | 0.00002 ppm DNase + 0.015% Cellulase | 326.890 | 40.27 | 3.19 |
| | 0.00002 ppm DNase + 0.15% Cellulase | 332.886 | 46.27 | 5.72 |

SEQUENCE LISTING

```
Sequence total quantity: 91
SEQ ID NO: 1                moltype = AA   length = 182
FEATURE                     Location/Qualifiers
source                      1..182
                            mol_type = protein
                            organism = Bacillus sp.
SEQUENCE: 1
LPPDLPSKST TQAQLNSLNV KNEESMSGYS REKFPHWISQ GDGCDTRQVI LKRDADNYSG   60
NCPVTSGKWY SYYDGITFND PSQLDIDHVV PLAEAWRSGA SSWSTAKRED FANDLNGPQL  120
IAVSASSNRS KGDQDPSTWQ PPRAGANCAY AKMWINTKYN WGLHLQSSEK TALQGMLNSC  180
SY                                                                 182

SEQ ID NO: 2                moltype = AA   length = 182
FEATURE                     Location/Qualifiers
source                      1..182
                            mol_type = protein
                            organism = Bacillus horikoshii
SEQUENCE: 2
LPPGTPTKSE AQNQLNSLTV KSEGSMTGYS RDLFPHWSGQ GNGCDTRQIV LQRDADYYTG   60
TCPTTSGKWY SYFDGVIVYS PSEIDIDHIV PLAEAWRSGA SSWTTEQRRA FANDLNGPQL  120
IAVTASVNRS KGDQDPSTWQ PPRAGARCAY AKWWINTKHR WNLHLQSSEK SSLQTMLNGC  180
AY                                                                 182

SEQ ID NO: 3                moltype = AA   length = 182
FEATURE                     Location/Qualifiers
source                      1..182
                            mol_type = protein
                            organism = Bacillus sp.
SEQUENCE: 3
LPPGTPSKSE AQSQLNALTV KPEDPMTGYS RDHFPHWISQ GNGCNTRQIV LQRDADYYSG   60
ACPVTTGKWY SYFDGVIVYS PSEIDIDHIV PLAEAWRSGA SSWTTEKRRS FANDLNGPQL  120
IAVTASVNRS KGDQDPSTWQ PPRAGARCAY AKWWINTKHR WGLHLQSSEK SSLQSMLNGC  180
AY                                                                 182

SEQ ID NO: 4                moltype = AA   length = 182
FEATURE                     Location/Qualifiers
source                      1..182
                            mol_type = protein
                            organism = Bacillus sp.
SEQUENCE: 4
LPPGTPSKSE AQSQLNALTV KPEDPMTGYS RDHFPHWISQ GNGCNTRQIV LQRDADYYSG   60
ACPVTTGKWY SYFDGVIVYS PSEIDIDHIV PLAEAWRSGA SSWTTEQRRS FANDLNGPQL  120
IAVTASVNRS KGDQDPSTWQ PPRAGARCAY AKWWINTKHR WGLHLQSSEK SSLQSMLNGC  180
AY                                                                 182

SEQ ID NO: 5                moltype = AA   length = 182
FEATURE                     Location/Qualifiers
source                      1..182
                            mol_type = protein
                            organism = Bacillus horikoshii
SEQUENCE: 5
LPPGTPSKSE AQSQLNSLTV KSEDPMTGYS RDHFPHWSGQ GNGCDTRQIV LQRDADYYSG   60
NCPVTSGKWY SYFDGVIVYS PSEIDIDHVV PLAEAWRSGA SSWTTEQRRS FANDLNGPQL  120
IAVTASVNRS KGDQDPSTWQ PPRAGARCAY AKWWINTKHR WNLHLQSSEK SALQTMLNGC  180
VY                                                                 182

SEQ ID NO: 6                moltype = AA   length = 182
FEATURE                     Location/Qualifiers
source                      1..182
                            mol_type = protein
                            organism = Bacillus horikoshii
SEQUENCE: 6
LPPGTPSKSE AQSQLNSLTV KTEDPMTGYS RDLFPHWSGQ GSGCDTRQIV LQRDADYFTG   60
TCPTTSGKWY SYFDGVIVYS PSEIDVDHIV PLAEAWRSGA SSWTTEQRRA FANDLTGPQL  120
IAVTASVNRS KGDQDPSTWQ PPRAGARCAY AKWWINTKHR WNLHLQSSEK SSLQTMLNGC  180
AY                                                                 182

SEQ ID NO: 7                moltype = AA   length = 182
FEATURE                     Location/Qualifiers
source                      1..182
                            mol_type = protein
                            organism = Bacillus sp.
SEQUENCE: 7
LPPGTPSKSE AQSQLNALTV KAEDPMTGYS RNLFPHWNSQ GNGCNTRQLV LQRDADYYSG   60
NCPVTSGRWY SYFDGVVVTS PSEIDIDHIV PLAEAWRSGA SSWTTEKRKE FANDLNGPQL  120
IAVTASVNRS KGDQDPSTWQ PPRAAARCGY AKWWINTKYR WDLSLQSSEK SSLQTMLNTC  180
SY                                                                 182
```

```
SEQ ID NO: 8              moltype = AA  length = 182
FEATURE                   Location/Qualifiers
source                    1..182
                          mol_type = protein
                          organism = Bacillus sp.
SEQUENCE: 8
LPPGTPSKSQ AQSQLNALTV KAEDPMTGYS RNLFPHWSSQ GNGCNTRQLV LQRDADYYSG    60
NCPVTSGRWY SYFDGVVVTS PSEIDIDHIV PLAEAWRSGA SSWTTEKRRE FANDLNGPQL   120
IAVTASVNRS KGDQDPSTWQ PPRVAARCGY AKWWINTKYR WDLSLQSSEK SSLQTMLNTC   180
SY                                                                 182

SEQ ID NO: 9              moltype = AA  length = 182
FEATURE                   Location/Qualifiers
source                    1..182
                          mol_type = protein
                          organism = Bacillus sp.
SEQUENCE: 9
LPPGTPSKSE AQSQLTSLTV KPEDPMTGYS RDHFPHWISQ GNGCNTRQIV LQRDADYYSG    60
NCPVTTGKWY SYFDGVIVYS PSEIDIDHIV PLAEAWRSGA SSWTAEQRRN FANDLNGPQL   120
IAVTASVNRS KGDQDPSTWQ PPRTGARCAY AKWWINTKYR WGLHLQSSEK SSLQSMLNGC   180
AY                                                                 182

SEQ ID NO: 10             moltype = AA  length = 183
FEATURE                   Location/Qualifiers
source                    1..183
                          mol_type = protein
                          organism = Bacillus sp.
SEQUENCE: 10
APPPGTPSKS TAQSQLNSLT VKSEGSMTGY SRDKFPHWIS QGDGCDTRQL VLKRDGDYYS    60
GNCPVTSGKW YSYYDGIAVY SPSEIDIDHI VPLAEAWRSG ASGWTTEKRQ NFANDLNGPQ   120
LIAVTASVNR SKGDQDPSTW QPPRSGSHCA YAKMWVNTKY RWGLHLQSAE KSALQSMLNA   180
CSY                                                                183

SEQ ID NO: 11             moltype = AA  length = 185
FEATURE                   Location/Qualifiers
source                    1..185
                          mol_type = protein
                          organism = Bacillus horneckiae
SEQUENCE: 11
ASAFPPGTPS KSTAQSQLNS LTVKSEGSMT GYSRDKFPHW ISQGDGCDTR QLVLKRDGDY    60
YSGNCPVTSG KWYSYYDGIT VYSPSEIDID HIVPLAEAWR SGASGWTTEK RQSFANDLNG   120
PQLIAVTASV NRSKGDQDPS TWQPPRSGSH CAYAKMWVNT KYRWGLHVQS AEKSALQSML   180
NACSY                                                              185

SEQ ID NO: 12             moltype = AA  length = 182
FEATURE                   Location/Qualifiers
source                    1..182
                          mol_type = protein
                          organism = Bacillus sp.
SEQUENCE: 12
FPPEIPSKST AQSQLNSLTV KSEDAMTGYS RDKFPHWISQ GDGCDTRQMV LKRDADYYSG    60
SCPVTSGKWY SYYDGITVYS PSEIDIDHIV PLAEAWRSGA SSWTTEKRRN FANDLNGPQL   120
IAVTASVNRS KGDQDPSTWQ PPRSGARCAY AKMWVNTKYR WGLHLQSAEK SGLESMLNTC   180
SY                                                                 182

SEQ ID NO: 13             moltype = AA  length = 182
FEATURE                   Location/Qualifiers
source                    1..182
                          mol_type = protein
                          organism = Bacillus cibi
SEQUENCE: 13
TPPGTPSKSA AQSQLNALTV KTEGSMSGYS RDLFPHWISQ GSGCDTRQVV LKRDADSYSG    60
NCPVTSGSWY SYYDGVTFTN PSDLDIDHIV PLAEAWRSGA SSWTTSKRQD FANDLSGPQL   120
IAVSASTNRS KGDQDPSTWQ PPRSGAACGY SKWWISTKYK WGLSLQSSEK TALQGMLNSC   180
SY                                                                 182

SEQ ID NO: 14             moltype = AA  length = 182
FEATURE                   Location/Qualifiers
source                    1..182
                          mol_type = protein
                          organism = Bacillus sp.
SEQUENCE: 14
FPPGTPSKST AQSQLNSLTV KSEGSMTGYS RDKFPHWIGQ GSGCDTRQLV LQRDADYYSG    60
SCPVTSGKWY SYYDGVTFYD PSDLDIDHVV PLAEAWRSGA SSWSTQKRKD FANDLSGPQL   120
IAVSASSNRS KGDQDPSTWQ PTRSGAACGY SKWWISTKHK WGLSLQSSEK NALQGMLNSC   180
VY                                                                 182

SEQ ID NO: 15             moltype = AA  length = 182
FEATURE                   Location/Qualifiers
```

```
source                  1..182
                        mol_type = protein
                        organism = Bacillus idriensis
SEQUENCE: 15
LPPGTPSKST AQSQLNALTV QTEGSMTGYS RDKFPHWISQ GNGCDTRQVV LQRDADYYSG   60
TCPVTSGKWY SYYDGVTLYN PSDLDIDHVV ALAEAWRSGA SSWTTDKRED FANDLSGTQL  120
IAVSASTNRS KGDQDPSTWQ PPRSGAACGY AKWWISTKYK WNLNLQSSEK TALQSMLNSC  180
SY                                                                182

SEQ ID NO: 16           moltype = AA  length = 182
FEATURE                 Location/Qualifiers
source                  1..182
                        mol_type = protein
                        organism = Bacillus algicola
SEQUENCE: 16
FPPGTPSKSE AQSQLNSLTV QSEGSMSGYS RDKFPHWIGQ GNGCDTRQLV LQRDADYYSG   60
DCPVTSGKWY SYFDGVTVYD PSDLDIDHMV PMAEAWRSGA SSWSTQKRED FANDLSGPHL  120
IAVTASSNRS KGDQDPSTWK PTRYGAHCGY AKWWINTKYV YDLTLQSSEK TELQSMLNTC  180
SY                                                                182

SEQ ID NO: 17           moltype = AA  length = 182
FEATURE                 Location/Qualifiers
source                  1..182
                        mol_type = protein
                        note = Enviromental sample J
                        organism = unidentified
SEQUENCE: 17
LPPNIPSKAD ALTKLNALTV QTEGPMTGYS RDLFPHWSSQ GNGCNTRHVV LKRDADSVVD   60
TCPVTTGRWY SYYDGLVFTS ASDIDIDHVV PLAEAWRSGA SSWTSTKRQS FANDLNGPQL  120
IAVSATSNRS KGDQDPSTWQ PPRAGARCAY AKMWVETKSR WGLTLQSSEK AALQTAINAC  180
SY                                                                182

SEQ ID NO: 18           moltype = AA  length = 182
FEATURE                 Location/Qualifiers
source                  1..182
                        mol_type = protein
                        organism = Bacillus vietnamensis
SEQUENCE: 18
FPPGTPSKST AQSQLNALTV KSESSMTGYS RDKFPHWIGQ RNGCDTRQLV LQRDADSYSG   60
SCPVTSGSWY SYYDGVTFTD PSDLDIDHVV PLAEAWRSGA SSWTTAKRED FANDLSGPQL  120
IAVSASSNRS KGDQDPSTWQ PPRSGAACGY SKWWISTKYK WGLSLQSSEK TALQGMLNSC  180
IY                                                                182

SEQ ID NO: 19           moltype = AA  length = 182
FEATURE                 Location/Qualifiers
source                  1..182
                        mol_type = protein
                        organism = Bacillus hwajinpoensis
SEQUENCE: 19
IPPGTPSKSA AQSQLDSLAV QSEGSMSGYS RDKFPHWIGQ GNGCDTRQLV LQRDADYYSG   60
DCPVTSGKWY SYFDGVQVYD PSYLDIDHMV PLAEAWRSGA SSWSTQKRED FANDLDGPHL  120
IAVTASSNRS KGDQDPSTWK PTRYSAHCGY AKWWINTKYV YDLNLQSSEK SALQSMLNTC  180
SY                                                                182

SEQ ID NO: 20           moltype = AA  length = 182
FEATURE                 Location/Qualifiers
source                  1..182
                        mol_type = protein
                        organism = Paenibacillus mucilaginosus
SEQUENCE: 20
LPPGTPSKST AQSQLNSLTV KSESTMTGYS RDKFPHWTSQ GGGCDTRQVV LKRDADYYSG   60
SCPVTSGKWY SYYDGITVYS PSEIDIDHIV PLAEAWRSGA SSWTTEKRQN FANDLGGPQL  120
IAVTASSNRA KGDQDPSTWK PTRSGAHCAY AKWWINTKYR WGLHLQSSEK TALQSMLNTC  180
SY                                                                182

SEQ ID NO: 21           moltype = AA  length = 182
FEATURE                 Location/Qualifiers
source                  1..182
                        mol_type = protein
                        organism = Bacillus indicus
SEQUENCE: 21
TPPGTPSKST AQTQLNALTV KTEGSMTGYS RDLFPHWISQ GSGCDTRQVV LKRDADYYSG   60
SCPVTSGKWY SYYDGVTFYD PSDLDIDHIV PLAEAWRSGA SSWTTSKRQD FANDLSGPQL  120
IAVSASTNRS KGDQDPSTWQ PPRAGAACGY SKWWISTKYK WGLSLQSSEK TALQGMLNSC  180
SY                                                                182

SEQ ID NO: 22           moltype = AA  length = 182
FEATURE                 Location/Qualifiers
source                  1..182
```

```
                          mol_type = protein
                          organism = Bacillus marisflavi
SEQUENCE: 22
TPPVTPSKAT SQSQLNGLTV KTEGAMTGYS RDKFPHWSSQ GGGCDTRQVV LKRDADSYSG        60
NCPVTSGSWY SYYDGVKFTN PSDLDIDHIV PLAEAWRSGA SSWTTAQREA FANDLSGSQL       120
IAVSASSNRS KGDQDPSTWQ PPRAGAKCGY AKWWISTKSK WNLSLQSSEK TALQGMLNSC       180
VY                                                                     182

SEQ ID NO: 23             moltype = AA  length = 184
FEATURE                   Location/Qualifiers
source                    1..184
                          mol_type = protein
                          organism = Bacillus luciferensis
SEQUENCE: 23
ASLPPGIPSL STAQSQLNSL TVKSEGSLTG YSRDVFPHWI SQGSGCDTRQ VVLKRDADYY        60
SGNCPVTSGK WYSYYDGVTV YSPSEIDIDH VVPLAEAWRS GASSWTTEKR QNFANDLNGP       120
QLIAVTASSN RSKGDQDPST WQPTRTGARC AYAKMWINTK YRWGLHLQSS EKSALQSMLN       180
TCSY                                                                   184

SEQ ID NO: 24             moltype = AA  length = 182
FEATURE                   Location/Qualifiers
source                    1..182
                          mol_type = protein
                          organism = Bacillus marisflavi
SEQUENCE: 24
TPPVTPSKET SQSQLNGLTV KTEGAMTGYS RDKFPHWSSQ GGGCDTRQVV LKRDADSYSG        60
NCPVTSGSWY SYYDGVKFTH PSDLDIDHIV PLAEAWRSGA SSWTTAQREA FANDLSGSQL       120
IAVSASSNRS KGDQDPSTWQ PPRAGAKCGY AKWWISTKSK WNLSLQSSEK TALQGMLNSC       180
VY                                                                     182

SEQ ID NO: 25             moltype = AA  length = 182
FEATURE                   Location/Qualifiers
source                    1..182
                          mol_type = protein
                          organism = Bacillus sp.
SEQUENCE: 25
LPSGIPSKST AQSQLNSLTV KSEGSMTGYS RDKFPHWISQ GGGCDTRQVV LKRDADYYSG        60
NCPVTSGKWY SYYDGISVYS PSEIDIDHVV PLAEAWRSGA SSWTTTKRQN FANDLNGPQL       120
IAVTASVNRS KGDQDPSTWQ PPRYGARCAY AKMWINTKYR WDLNLQSSEK SSLQSMLDTC       180
SY                                                                     182

SEQ ID NO: 26             moltype = AA  length = 191
FEATURE                   Location/Qualifiers
source                    1..191
                          mol_type = protein
                          organism = Pyrenochaetopsis sp.
SEQUENCE: 26
LPSPLLIARS PPNIPSATTA KTQLAGLTVA PQGPQTGYSR DLFPHWITQS GTCNTREVVL        60
KRDGTNVVTN SACASTSGSW LSPYDGKTWD SASDIQIDHL VPLSNAWKSG AAAWTTAQRQ       120
AFANDLTHPQ LVAVTGSVNE SKGDDGPEDW KPPLASYYCT YASMWTAVKS NYKLTITSAE       180
KSALTSMLAT C                                                           191

SEQ ID NO: 27             moltype = AA  length = 190
FEATURE                   Location/Qualifiers
source                    1..190
                          mol_type = protein
                          organism = Vibrissea flavovirens
SEQUENCE: 27
TPLPIIARTP PNIPTTATAK SQLAALTVAA AGPQTGYSRD LFPTWITISG TCNTRETVLK        60
RDGTNVVVDS ACVATSGSWY SPYDGATWTA ASDVDIDHMV PLSNAWKSGA SAWTTAQRQT       120
FANDLTNPQL LAVTDNVNQA KGDSGPEDWK PSLTSYWCTY AKMWVKVKTV YDLTITSAEK       180
TALTTMLNTC                                                             190

SEQ ID NO: 28             moltype = AA  length = 192
FEATURE                   Location/Qualifiers
source                    1..192
                          mol_type = protein
                          organism = Setosphaeria rostrata
SEQUENCE: 28
APTSSPLVAR APPNVPSKAE ATSQLAGLTV APQGPQTGYS RDLFPHWITQ SGTCNTRETV        60
LKRDGTNVVT NSACASTSGS WFSPYDGATW TAASDVDIDH MVPLSNAWKS GAASWTTARR       120
QAFANDLTNP QLLAVTDNVN QAKGDKGPED WKPPLTSYYC TYSKMWIKVK SVWGLTITSA       180
EKSALTSMLA TC                                                          192

SEQ ID NO: 29             moltype = AA  length = 192
FEATURE                   Location/Qualifiers
source                    1..192
                          mol_type = protein
                          organism = Endophragmiella valdina
```

```
SEQUENCE: 29
APVPGHLMPR APPNVPTTAA AKTALAGLTV QAQGSQTGYS RDLFPHWITQ SGTCNTREVV    60
LKRDGTNVVT DSACAATSGT WVSPYDGATW TAASDVDIDH MVPLSNAWKS GAASWTTAQR   120
QAFANDLTNP QLLAVTDNVN QSKGDKGPED WKPPLTSYYC TYAKMWVKVK SVYSLTITSA   180
EKTALTSMLN TC                                                      192

SEQ ID NO: 30           moltype = AA  length = 190
FEATURE                 Location/Qualifiers
source                  1..190
                        mol_type = protein
                        organism = Corynespora cassiicola
SEQUENCE: 30
LPAPLVPRAP PGIPTTSAAR SQLAGLTVAA QGPQTGYSRD LFPHWITQSG SCNTREVVLA    60
RDGTGVVQDS SCAATSGTWR SPFDGATWTA ASDVDIDHMV PLSNAWKSGA ASWTTSRRQA   120
FANDLTNPQL IAVTDNVNQS KGDKGPEDWK PPLTSYYCTY AKMWVRVKSV YSLTITSAEK   180
SALTSMLDTC                                                         190

SEQ ID NO: 31           moltype = AA  length = 192
FEATURE                 Location/Qualifiers
source                  1..192
                        mol_type = protein
                        organism = Paraphoma sp.
SEQUENCE: 31
APAPVHLVAR APPNVPTAAQ AQTQLAGLTV AAQGPQTGYS RDLFPHWITQ SGACNTRETV    60
LKRDGTGVVQ DSACAATSGT WKSPYDGATW TAASDVDIDH MVPLSNAWKS GAASWTTARR   120
QAFANDLTNP QLLAVTDNVN QAKGDKGPED WKPPLTSYYC IYARMWIKVK SVYSLTITSA   180
EKSALTSMLG TC                                                      192

SEQ ID NO: 32           moltype = AA  length = 186
FEATURE                 Location/Qualifiers
source                  1..186
                        mol_type = protein
                        organism = Monilinia fructicola
SEQUENCE: 32
TPVPAPTGIP STSVANTQLA ALTVAAAGSQ DGYSRDLFPH WITISGACNT RETVLKRDGT    60
NVVVNSACAA TSGTWVSPYD GATWTAASDV DIDHLVPLSN AWKAGASSWT TAQRQAFAND   120
LVNPQLLAVT DSVNQGKSDS GPEAWKPSLK SYWCTYAKMW IKVKYVYDLT ITSAEKSALV   180
TMMDTC                                                             186

SEQ ID NO: 33           moltype = AA  length = 190
FEATURE                 Location/Qualifiers
source                  1..190
                        mol_type = protein
                        organism = Curvularia lunata
SEQUENCE: 33
APAPLSARAP PNIPSKADAT SQLAGLTVAA QGPQTGYSRD LFPHWITQSG TCNTRETVLK    60
RDGTNVVTSS SCAATSGTWF SPYDGATWTA ASDVDIDHVV PLSNAWKSGA ASWTTARRQA   120
FANDLTNPQL IAVTDSVNQA KGDKGPEDWK PPLSSYYCTY SKMWIKVKSV YGLTVTSAEK   180
SALSSMLATC                                                         190

SEQ ID NO: 34           moltype = AA  length = 191
FEATURE                 Location/Qualifiers
source                  1..191
                        mol_type = protein
                        organism = Penicillium reticulisporum
SEQUENCE: 34
LPAPEALPAP PGVPSASTAQ SELAALTVAA QGSQDGYSRS KFPHWITQSG SCDTRDVVLK    60
RDGTNVVQSA SGCTITSGKW VSPYDGATWT ASSDVDIDHL VPLSNAWKSG ASGWTTAARQ   120
AFANDLTNPQ LLVVTDNVNE SKGDKGPEEW KPPLTSYYCT YAEMWVKVKS VYKLTITSAE   180
KSALTSMLST C                                                       191

SEQ ID NO: 35           moltype = AA  length = 191
FEATURE                 Location/Qualifiers
source                  1..191
                        mol_type = protein
                        organism = Penicillium quercetorum
SEQUENCE: 35
LPAPEPAPSP PGIPSASTAR SELASLTVAP QGSQDGYSRA KFPHWIKQSG SCDTRDVVLE    60
RDGTNVVQSS TGCTITGGTW VSPYDGATWT ASSDVDIDHL VPLSNAWKSG ASAWTTAQRQ   120
AFANDLTNPQ LVAVTDNVNE AKGDKGPEEW KPPLTSYYCT YAEMWVKVKS VYKLTITSAE   180
KSALSSMLNT C                                                       191

SEQ ID NO: 36           moltype = AA  length = 192
FEATURE                 Location/Qualifiers
source                  1..192
                        mol_type = protein
                        organism = Setophaeosphaeria sp.
SEQUENCE: 36
LPAPVTLEAR APPNIPSTAS ANTLLAGLTV AAQGSQTGYS RDLFPHWITQ SGTCNTRETV    60
```

```
LKRDGTGVVT DSACASTSGS WYSVYDGATW TAASDVDIDH VVPLSNAWKS GAASWTTARR    120
QSFANDLTNP QLIAVTDNVN QAKGDKGPED WKPPLTSYYC TYAKMWVKVK SVYSLTITSA    180
EKTALTSMLN TC                                                       192

SEQ ID NO: 37           moltype = AA  length = 192
FEATURE                 Location/Qualifiers
source                  1..192
                        mol_type = protein
                        organism = Alternaria sp.
SEQUENCE: 37
LPAPVTLEAR APPNIPTTAA AKTQLAGLTV AAQGPQTGYS RDLFPHWITQ SGTCNTRETV     60
LKRDGTGVVT DSACASTSGS WFSVYDGATW TAASDVDIDH VVPLSNAWKS GAASWTTARR    120
QSFANDLTNP QLIAVTDNVN QAKGDKGPED WKPPLTSYYC TYAKMWVKVK SVYALTITSA    180
EKTALTSMLN TC                                                       192

SEQ ID NO: 38           moltype = AA  length = 192
FEATURE                 Location/Qualifiers
source                  1..192
                        mol_type = protein
                        organism = Alternaria sp.
SEQUENCE: 38
LPAPVTLEAR APPNIPTTAA AKTQLAGLTV AAQGPQTGYS RDLFPHWITQ SGSCNTREVV     60
LQRDGTGVVT DSACAATSGS WYSVYDGATW TAASDVDIDH MVPLSNAWKS GAASWTTARR    120
QAFANDLTNP QLLAVTDNVN QAKGDKGPED WKPPLTSYYC TYAKMWVKVK SVYALTITSA    180
EKTALTSMLN TC                                                       192

SEQ ID NO: 39           moltype = AA  length = 186
FEATURE                 Location/Qualifiers
source                  1..186
                        mol_type = protein
                        organism = Trichoderma reesei
SEQUENCE: 39
APLPAPPGIP SEDTARTQLA GLTVAVVGSG TGYSRDLFPT WDAISGNCNA REYVLKRDGE     60
GVQVNNACEA QSGSWISPYD NASFTNASSL DIDHMVPLKN AWISGASTWT TAQREALAND    120
VSRPQLWAVS ASSNRSKGDR SPDQWKPPLT SFYCTYAKSW IDVKSYYKLT ITSAEKTALS    180
SMLDTC                                                              186

SEQ ID NO: 40           moltype = AA  length = 188
FEATURE                 Location/Qualifiers
source                  1..188
                        mol_type = protein
                        organism = Chaetomium thermophilum
SEQUENCE: 40
APAPQPTPPG IPSRSTAQSY LNSLTVAASY DDGNYNRDLF PHWNTVSGTC NTREYVLKRD     60
GSNVVTNSAC QATSGTWYSP YDGATWTAAS DIDIDHMVPL KNAWISGANT WSSSKRSSFA    120
NDINSPQLWA VTDSVNQSKG DKSPDKWKPP LTTFYCTYAK SWITVKYNYN LTITSAEKSA    180
LQNMINTC                                                            188

SEQ ID NO: 41           moltype = AA  length = 190
FEATURE                 Location/Qualifiers
source                  1..190
                        mol_type = protein
                        organism = Scytalidium thermophilum
SEQUENCE: 41
LPAPAPMPTP PGIPSKSTAQ SQLNALTVKA SYDDGKYKRD LFPHWNTVSG TCNTREYVLK     60
RDGVNVVTNS ACAATSGTWY SPFDGATWTA ASDVDIDHMV PLKNAWISGA NNWTSTKRTQ    120
FANDINLPQL WAVTDDVNQA KGDKSPDKWK PPLTSFYCTY AKSWITVKYN YGLSITSAEK    180
SALTSMINTC                                                          190

SEQ ID NO: 42           moltype = AA  length = 186
FEATURE                 Location/Qualifiers
source                  1..186
                        mol_type = protein
                        organism = Metapochonia suchlasporia
SEQUENCE: 42
VPVPAPPGIP STSTAKTLLA GLKVAVPLSG DGYSREKFPL WETIQGTCNA REFVLKRDGT     60
DVKTNNACVA ESGNWVSPYD GVKFTAARDL DIDHMVPLKN AWISGASQWT TERRKALAND    120
ITRPQLWAVS AHANRGKSDD SPDEWKPPLK TFWCTYAKSW VQVKSFYELT ITDAEKGALA    180
GMLDSC                                                              186

SEQ ID NO: 43           moltype = AA  length = 198
FEATURE                 Location/Qualifiers
source                  1..198
                        mol_type = protein
                        organism = Daldinia fissa
SEQUENCE: 43
APAPIPVAEP APMPMPTPPG IPSASSAKSQ LASLTVKAAV DDGGYQRDLF PTWDTITGTC     60
NTREYVLKRD GANVQVGSDC YPTSGTWTSP YDGGKWTSPS DVDIDHMVPL KNAWVSGANK    120
WTTAKREQFA NDVDRPQLWA VTDNVNSSKG DKSPDTWKPP LTSFYCTYAS AYVAVKSYWG    180
```

```
LTITSAEKSA LSDMLGTC                                                    198

SEQ ID NO: 44           moltype = AA  length = 188
FEATURE                 Location/Qualifiers
source                  1..188
                        mol_type = protein
                        organism = Acremonium sp.
SEQUENCE: 44
LPLQSRDPPG IPSTATAKSL LNGLTVKAWS NEGTYDRDLF PHWQTIEGTC NAREYVLKRD        60
GQNVVVNSAC TAQSGTWKSV YDGETTNSAS DLDIDHMIPL KNAWISGAAT WTTAQRTSFA       120
NDISSPQLWA VTAGVNRSKS DRSPDTWVPP LASFHCTYGK AWVQVKSKWA LSITSAEKSA       180
LTGLLNKC                                                               188

SEQ ID NO: 45           moltype = AA  length = 182
FEATURE                 Location/Qualifiers
source                  1..182
                        mol_type = protein
                        organism = Acremonium dichromosporum
SEQUENCE: 45
IPPGIPSEAT ARSLLSSLTV APTVDDGTYD RDLFPHWSSV EGNCNAREFV LRRDGDGVSV        60
GNDCYPTAGT WTCPYDGKRH SVPSDVSIDH MVPLHNAWMT GASEWTTAER EAFANDIDGP       120
QLWAVTSTTN SQKGSDAPDE WQPPQTSIHC KYAAAWIQVK STYDLTVSSA EQAALEEMLG       180
RC                                                                     182

SEQ ID NO: 46           moltype = AA  length = 188
FEATURE                 Location/Qualifiers
source                  1..188
                        mol_type = protein
                        organism = Sarocladium sp.
SEQUENCE: 46
VPIPLPDPPG IPSSSTANTL LAGLTVRASS NEDTYNRDLF PHWVAISGNC NAREYVLRRD        60
GTNVVVNTAC VPQSGTWRSP YDGESTTNAS DLDIDHMVPL KNAWISGAAS WTTAKRQDFA       120
NDVSGPQLWA VTAGVNRSKG DKSPDSWVPP LASFHCTYAR SWIQVKSSWA LSVTSAEKAA       180
LTDLLSTC                                                               188

SEQ ID NO: 47           moltype = AA  length = 186
FEATURE                 Location/Qualifiers
source                  1..186
                        mol_type = protein
                        organism = Metarhizium sp.
SEQUENCE: 47
VPVPAPPGIP TASTARTLLA GLKVATPLSG DGYSRTLFPT WETIEGTCNA REFVLKRDGT        60
DVQTNTACVA QSGNWVSPYD GVAFTAASDL DIDHMVPLKN AWISGASQWT TDKRKGLAND       120
ITRPQLWAVS AHANRAKGDS SPDEWKPPLK TFWCTYARSW VQVKSYYALT ITDAEKGALS       180
GMLDSC                                                                 186

SEQ ID NO: 48           moltype = AA  length = 188
FEATURE                 Location/Qualifiers
source                  1..188
                        mol_type = protein
                        organism = Acremonium sp.
SEQUENCE: 48
APIAVRDPPG IPSASTANTL LAGLTVRASS NEDSYDRNLF PHWSAISGNC NAREFVLERD        60
GTNVVVNNAC VAQSGTWRSP YDGETTGNAS DLDIDHMVPL KNAWISGASS WSTTRRQEFA       120
NDVSGPQLWA VTAGVNRSKG DRSPDSWVPP LASFHCTYAK SWVQVKSSWS LSVTSAEKAA       180
LSDLLGTC                                                               188

SEQ ID NO: 49           moltype = AA  length = 186
FEATURE                 Location/Qualifiers
source                  1..186
                        mol_type = protein
                        organism = Isaria tenuipes
SEQUENCE: 49
APVPEPPGIP STSTAQSDLN SLQVAASGSG DGYSRAEFPH WVSVEGSCDS REYVLKRDGQ        60
DVQADSSCKI TSGTWVSPYD ATTWTNSSKV DIDHLVPLKN AWISGASSWT KAQRQDFAND       120
IKRPQLYAVS ENANRSKGDR SPDGWKPPLK SFYCTYAKSW VAVKSYYKLT ITSAEKSALG       180
DMLDTC                                                                 186

SEQ ID NO: 50           moltype = AA  length = 184
FEATURE                 Location/Qualifiers
source                  1..184
                        mol_type = protein
                        organism = Scytalidium circinatum
SEQUENCE: 50
APPGIPSAST ASSLLGELAV AEPVDDGSYD RDLFPHWEPI PGETACSARE YVLRRDGTGV        60
ETGSDCYPTS GTWSSPYDGG SWTAPSDVDI DHMVPLKNAW ISGASEWTTA EREAFANDID       120
GPQLWAVTDE VNQSKSDQSP DEWKPPLSSF YCTYACAWIQ VKSTYSLSIS SAEQAALEDM       180
LGSC                                                                   184
```

```
SEQ ID NO: 51            moltype = AA  length = 186
FEATURE                  Location/Qualifiers
source                   1..186
                         mol_type = protein
                         organism = Metarhizium lepidiotae
SEQUENCE: 51
VPVPAPPGIP TASTARTLLA GLKVATPLSG DGYSRTLFPT WETIEGTCNA REFVLKRDGT    60
DVQTNTACVA ESGNWVSPYD GVSFTAASDL DIDHMVPLKN AWISGASQWT TDKRKDLAND   120
ITRPQLWAVS AHANRSKGDS SPDEWKPPLQ TFWCTYSKSW IQVKSHYSLT ITDAEKGALS   180
GMLDSC                                                              186

SEQ ID NO: 52            moltype = AA  length = 226
FEATURE                  Location/Qualifiers
source                   1..226
                         mol_type = protein
                         organism = Thermobispora bispora
SEQUENCE: 52
LDIADGRPAG GKAAEAATGT SPLANPDGTR PGLAAITSAD ERAEARALIE RLRTKGRGPK    60
TGYEREKFGY AWADSVDGIP FGRNGCDTRN DVLKRDGQRL QFRSGSDCVV ISMTLFDPYT   120
GKTIEWTKQN AAEVQIDHVV PLSYSWQMGA SRWSDEKRRQ LANDPLNLMP VDGATNSRKG   180
DSGPASWLPP RREIRCAYVV RFAQVALKYD LPVTTADKET MLQQCS                  226

SEQ ID NO: 53            moltype = AA  length = 191
FEATURE                  Location/Qualifiers
source                   1..191
                         mol_type = protein
                         organism = Sporormia fimetaria
SEQUENCE: 53
LPAPVLEKRT PPNIPSTSTA QSLLSGLTVA PQGSQTGYSR DLFPHWITVS GTCNTRETVL    60
KRDGSNVVTD SACASVSGSW YSTYDGATWT AASDVDHV VPLSNAWKSG AASWTTARRQ    120
AFANDLTNPQ LIAVTDNVNQ AKGDQGPESW KPPLTSYYCT YAKMWVKVKS VYSLTVTSAE   180
KSALSSMLGT C                                                        191

SEQ ID NO: 54            moltype = AA  length = 193
FEATURE                  Location/Qualifiers
source                   1..193
                         mol_type = protein
                         organism = Pycnidiophora cf.dispera
SEQUENCE: 54
LPAPAPVLVA REPPNIPSTS SAQSMLSGLT VKAQGPQDGY SRDLFPHWIT ISGTCNTRET    60
VLKRDGTNVV TNSACASTSG SWYSPYDGAT WTAASDVDID HIVPLSNAWK SGAASWTTSR   120
RQQFANDLTN PQLIAVTDSV NQAKGDKGPE DWKPSRTSYH CTYAKMWIKV KSVYSLTVTS   180
AEKSALTTML NTC                                                      193

SEQ ID NO: 55            moltype = AA  length = 199
FEATURE                  Location/Qualifiers
source                   1..199
                         mol_type = protein
                         note = Enviromental sample D
                         organism = unidentified
SEQUENCE: 55
DTDPEPVAGS ALEALAGLEV KGPGPDTGYE RALFGPPWAD VDGNGCDTRN DILARDLTDL    60
TFSTRGDVCE VRTGTFDDPY TGETIDFRRG NATSAAVQID HVVPLLDAWR KGARAWDDET   120
RRQFANDPLN LLASDGPANQ SKGARDASAW LPPNHAFRCP YVARQIAVKA AYELSVTPSE   180
SEAMARVLAD CPAEPLPAG                                                199

SEQ ID NO: 56            moltype = AA  length = 199
FEATURE                  Location/Qualifiers
source                   1..199
                         mol_type = protein
                         note = Enviromental sample O
                         organism = unidentified
SEQUENCE: 56
DDEPEPARGS ALEALARLEV VGPGPDTGYE RELFGPAWAD VDGNGCDTRN DILARDLTDL    60
TFSTRGEVCE VRTGTFQDPY TGETIDFRRG NATSMAVQID HVVPLMDAWR KGARAWDDET   120
RRQFANDPLN LLASDGPANQ SKGARDASAW LPPNHAFRCP YVARQIAVKT AYELSVTPSE   180
SEAMARVLED CPAEPVPAG                                                199

SEQ ID NO: 57            moltype = AA  length = 186
FEATURE                  Location/Qualifiers
source                   1..186
                         mol_type = protein
                         organism = Clavicipitaceae sp.
SEQUENCE: 57
VPVPAPPGIP STSTAKTLLA GLKVATPLSG DGYSRDKFPT WETIQGTCNA REFVIKRDGT    60
DVKTNSACVA ESGNWVSPYD GVKFTAARDL DIDHMVPLKN AWISGASQWT TEQRKALAND   120
ITRPQLWAVS AHANRGKSDD SPDEWKPPLK TFWCTYAKSW VQVKSFYKLT ITDTEKGALA   180
GMLDTC                                                              186
```

```
SEQ ID NO: 58              moltype = AA  length = 187
FEATURE                    Location/Qualifiers
source                     1..187
                           mol_type = protein
                           organism = Westerdykella sp.
SEQUENCE: 58
FPAPASVLEA RAPPNIPSAS TAQSLLVGLT VQPQGPQDGY SRDLFPHWIT ISGTCNTRET    60
VLKRDGSNVV TNSACAATSG TWYSPYDGAT WTSASDVDID HLVPLSNAWK SGAASWTTAK   120
RQQFANDLTN PQLLAVTDRV NQAKGDKGPE AWKPSLASYH CTYAKMWVKV KSKDVRLTGN   180
WTKDDGW                                                             187

SEQ ID NO: 59              moltype = AA  length = 194
FEATURE                    Location/Qualifiers
source                     1..194
                           mol_type = protein
                           organism = Humicolopsis cephalosporioides
SEQUENCE: 59
APTPAPVELE RRTPPNIPTT ASAKSLLAGL TVAAQGPQTG YSRDLFPHWI TISGSCNTRE    60
TVLKRDGTGV VTDSACASTA GSWYSPYDGA TWTAASDVDI DHMVPLSNAW KSGAAQWTTA   120
RRQDFANDLT NPQLFAVTDN VNQEKGDKGP EDWKPSLTSY YCTYAKAWVK VKSVWALTIT   180
SAEKSALTTM LNTC                                                     194

SEQ ID NO: 60              moltype = AA  length = 190
FEATURE                    Location/Qualifiers
source                     1..190
                           mol_type = protein
                           organism = Neosartorya massa
SEQUENCE: 60
IPAPVALPTP PGIPSAATAE SELAALTVAA QGSSSGYSRD LFPHWISQGG SCNTREVVLA    60
RDGSGVVKDS NCYPTSGSWY SPYDGATWTQ ASDVDIDHVV PLANAWRSGA SKWTTSQRQA   120
FANDLTNPQL MAVTDNVNQA KGDDGPEAWK PPLTSYYCTY AKMWVRVKYV YDLTITSAEK   180
SALVSMLDTC                                                          190

SEQ ID NO: 61              moltype = AA  length = 191
FEATURE                    Location/Qualifiers
source                     1..191
                           mol_type = protein
                           organism = Roussoella intermedia
SEQUENCE: 61
APTPALLPRA PPNIPSTATA KSQLAALTVA AQGPQDGYSR DLFPHWITQS GSCNTREVVL    60
KRDGTNVVQD SSCAATSGTW VSPFDGATWT AASDVDIDHL VPLSNAWKSG AASWTTARRQ   120
SFANDLTNPQ LLAVTDEVNQ AKGDKGPEAW KPPLASYHCT YAKMWVKVKS TYSLTITSAE   180
KSALTTMLNT C                                                        191

SEQ ID NO: 62              moltype = AA  length = 191
FEATURE                    Location/Qualifiers
source                     1..191
                           mol_type = protein
                           organism = Pleosporales sp.
SEQUENCE: 62
LPTPSLVKRT PPNIPSTTSA KSLLAGLTVA AQGPQDGYSR DLFPHWITIS GTCNTRETVL    60
KRDGTNVVTD SACASTSGSW YSTYDGATWT AASDVDIDHV VPLSNAWKSG AASWTTARRQ   120
SFANDLTNPQ LIAVTDSVNQ SKGDKGPESW KPPLTSYHCT YAKMWVKVKD VYSLTVTSAE   180
KSALTTMLNT C                                                        191

SEQ ID NO: 63              moltype = AA  length = 192
FEATURE                    Location/Qualifiers
source                     1..192
                           mol_type = protein
                           organism = Phaeosphaeria sp.
SEQUENCE: 63
LPAPIHLTAR APPNIPSASE ARTQLAGLTV AAQGPQDGYS RDLFPHWITQ SGTCNTRETV    60
LKRDGTNVVT NSACASTSGS WFSPYDGATW TAASDVDIDH MVPLSNAWKS GAASWTTARR   120
QAFANDLTNP QLLAVTDNVN QAKGDKGPED WKPPLTSYYC TYARMWVKVK SVYALTVTSA   180
EKSALTSMLG TC                                                       192

SEQ ID NO: 64              moltype = AA  length = 189
FEATURE                    Location/Qualifiers
source                     1..189
                           mol_type = protein
                           organism = Didymosphaeria futilis
SEQUENCE: 64
LPTPNTLEAR APPNIPSTSA AQSQLSALTV AAQGPQTGYS RDLFPHWITQ SGTCNTRETV    60
LKRDGTNVLT DSACASTSGS WKSPYDGATW TAASDVDIDH VVPLSNAWKS GAASWTTARR   120
QSFANDLTNP QLIAVTDNVN QAKGDKGPED WKPPLTSYYC TYAKMWVKVK SVYSLTITSA   180
EKSALTMLA                                                           189

SEQ ID NO: 65              moltype = AA  length = 109
FEATURE                    Location/Qualifiers
```

```
                            source            1..109
                                              mol_type = protein
                                              organism = Bacillus licheniformis
SEQUENCE: 65
ARYDDILYFP ASRYPETGAH ISDAIKAGHS DVCTIERSGA DKRRQESLKG IPTKPGFDRD    60
EWPMAMCEEG GKGASVRYVS SSDNRGAGSW VGNRLSGFAD GTRILFIVQ               109

SEQ ID NO: 66               moltype = AA   length = 110
FEATURE                     Location/Qualifiers
source                      1..110
                            mol_type = protein
                            organism = Bacillus subtilis
SEQUENCE: 66
ASSYDKVLYF PLSRYPETGS HIRDAIAEGH PDICTIDRDG ADKRREESLK GIPTKPGYDR    60
DEWPMAVCEE GGAGADVRYV TPSDNRGAGS WVGNQMSSYP DGTRVLFIVQ              110

SEQ ID NO: 67               moltype = AA   length = 221
FEATURE                     Location/Qualifiers
source                      1..221
                            mol_type = protein
                            organism = Aspergillus oryzae
SEQUENCE: 67
VPVNPEPDAT SVENVALKTG SGDSQSDPIK ADLEVKGQSA LPFDVDCWAI LCKGAPNVLQ    60
RVNEKTKNSN RDRSGANKGP FKDPQKWGIK ALPPKNPSWS AQDFKSPEEY AFASSLQGGT   120
NAILAPVNLA SQNSQGGVLN GFYSANKVAQ FDPSKPQQTK GTWFQITKFT GAAGPYCKAL   180
GSNDKSVCDK NKNIAGDWGF DPAKWAYQYD EKNNKFNYVG K                      221

SEQ ID NO: 68               moltype = AA   length = 188
FEATURE                     Location/Qualifiers
source                      1..188
                            mol_type = protein
                            organism = Trichoderma harzianum
SEQUENCE: 68
APAPMPTPPG IPTESSARTQ LAGLTVAVAG SGTGYSRDLF PTWDAISGNC NAREYVLKRD    60
GEGVQVNNAC ESQSGTWISP YDNASFTNAS SLDIDHMVPL KNAWISGASS WTTAQREALA   120
NDVSRPQLWA VSASANRSKG DRSPDQWKPP LTSFYCTYAK SWIDVKSFYK LTITSAEKTA   180
LSSMLDTC                                                           188

SEQ ID NO: 69               moltype =     length =
SEQUENCE: 69
000

SEQ ID NO: 70               moltype =     length =
SEQUENCE: 70
000

SEQ ID NO: 71               moltype =     length =
SEQUENCE: 71
000

SEQ ID NO: 72               moltype =     length =
SEQUENCE: 72
000

SEQ ID NO: 73               moltype = AA   length = 7
FEATURE                     Location/Qualifiers
source                      1..7
                            mol_type = protein
                            organism = synthetic construct
VARIANT                     1
                            note = X=D, M or L
VARIANT                     2
                            note = X=S or T
VARIANT                     7
                            note = X=D or N
SEQUENCE: 73
XXGYSRX                                                              7

SEQ ID NO: 74               moltype = AA   length = 8
FEATURE                     Location/Qualifiers
source                      1..8
                            mol_type = protein
                            organism = synthetic construct
VARIANT                     3
                            note = X=any amino acid
SEQUENCE: 74
ASXNRSKG                                                             8

SEQ ID NO: 75               moltype = AA   length = 8
```

-continued

```
FEATURE              Location/Qualifiers
source               1..8
                     mol_type = protein
                     organism = synthetic construct
VARIANT              1
                     note = X=V or I
VARIANT              4
                     note = X=S or A
SEQUENCE: 75
XPLXNAWK                                                                   8

SEQ ID NO: 76        moltype = AA  length = 4
FEATURE              Location/Qualifiers
REGION               1..4
                     note = Motif
source               1..4
                     mol_type = protein
                     organism = synthetic construct
SEQUENCE: 76
NPQL                                                                       4

SEQ ID NO: 77        moltype =     length =
SEQUENCE: 77
000

SEQ ID NO: 78        moltype =     length =
SEQUENCE: 78
000

SEQ ID NO: 79        moltype = AA  length = 269
FEATURE              Location/Qualifiers
source               1..269
                     mol_type = protein
                     organism = Bacillus lentus
SEQUENCE: 79
AQSVPWGISR VQAPAAHNRG LTGSGVKVAV LDTGISTHPD LNIRGGASFV PGEPSTQDGN   60
GHGTHVAGTI AALNNSIGVL GVAPSAELYA VKVLGASGSG SVSSIAQGLE WAGNNGMHVA  120
NLSLGSPSPS ATLEQAVNSA TSRGVLVVAA SGNSGAGSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 80        moltype = AA  length = 275
FEATURE              Location/Qualifiers
source               1..275
                     mol_type = protein
                     organism = Bacillus amyloliquefaciens
SEQUENCE: 80
AQSVPYGVSQ IKAPALHSQG YTGSNVKVAV IDSGIDSSHP DLKVAGGASM VPSETNPFQD   60
NNSHGTHVAG TVAALNNSIG VLGVAPSASL YAVKVLGADG SGQYSWIING IEWAIANNMD  120
VINMSLGGPS GSAALKAAVD KAVASGVVVV AAAGNEGTSG SSSTVGYPGK YPSVIAVGAV  180
DSSNQRASFS SVGPELDVMA PGVSIQSTLP GNKYGAYNGT SMASPHVAGA AALILSKHPN  240
WTNTQVRSSL ENTTTKLGDS FYYGKGLINV QAAAQ                             275

SEQ ID NO: 81        moltype = AA  length = 311
FEATURE              Location/Qualifiers
source               1..311
                     mol_type = protein
                     organism = Bacillus subtilis
SEQUENCE: 81
AVPSTQTPWG IKSIYNDQSI TKTTGGSGIK VAVLDTGVYT SHLDLAGSAE QCKDFTQSNP   60
LVDGSCTDRQ GHGTHVAGTV LAHGGSNGQG VYGVAPQAKL WAYKVLGDNG SGYSDDIAAA  120
IRHVADEASR TGSKVVINMS LGSSAKDSLI ASAVDYAYGK GVLIVAAAGN SGSGSNTIGF  180
PGGLVNAVAV AALENVQQNG TYRVADFSSR GNPATAGDYI IQERDIEVSA PGASVESTWY  240
TGGYNTISGT SMATPHVAGL AAKIWSANTS LSHSQLRTEL QNRAKVYDIK GGIGAGTGDD  300
YASGFGYPRV K                                                       311

SEQ ID NO: 82        moltype = AA  length = 298
FEATURE              Location/Qualifiers
source               1..298
                     mol_type = protein
                     organism = Bacillus bogoriensis
SEQUENCE: 82
ANSGFYVSGT TLYDANGNPF VMRGINHGHA WYKDQATTAI EGIANTGANT VRIVLSDGGQ   60
WTKDDIHTVR NLISLAEDNH LVAVLEVHDA TGYDSIASLN RAVDYWIEMR SALIGKEDTV  120
IININANEWFG SWEGDAWADG YKQAIPRLRN AGLNHTLMVD AAGWGQFPQS IHDYGREVFN  180
ADPQRNTMFS IHMYEYAGGN ASQVRTNIDR VLNQDLALVI GEFGHRHTNG DVDEATIMSY  240
SEQRGVGWLA WSWKGNGPEW EYLDLSNDWA GNNLTAWGNT IVNGPYGLRE TSRLSTVF    298

SEQ ID NO: 83        moltype = AA  length = 278
```

```
FEATURE                 Location/Qualifiers
source                  1..278
                        mol_type = protein
                        organism = Thielavia terrestris
SEQUENCE: 83
ASGSGQSTRY WDCCKPSCAW PGKAAVSQPV YACDANFQRL SDFNVQSGCN GGSAYSCADQ    60
TPWAVNDNLA YGFAATSIAG GSESSWCCAC YALTFTSGPV AGKTMVVQST STGGDLGSNQ   120
FDIAMPGGGV GIFNGCSSQF GGLPGAQYGG ISSRDQCDSF PAPLKPGCQW RFDWFQNADN   180
PTFTFQQVQC PAEIVARSGC KRNDDSSFPV FTPPSGGNGG TGTPTSTAPG SGQTSPGGGS   240
GCTSQKWAQC GGIGFSGCTT CVSGTTCQKL NDYFSQCL                          278

SEQ ID NO: 84           moltype = AA  length = 470
FEATURE                 Location/Qualifiers
source                  1..470
                        mol_type = protein
                        organism = Humicola insolens
SEQUENCE: 84
MRSSPLLRSA VVAALPVLAL AADGRSTRYW DCCKPSCGWA KKAPVNQPVF SCNANFQRIT    60
DFDAKSGCEP GGVAYSCADQ TPWAVNDDFA LGFAATSIAG SNEAGWCCAC YELTFTSGPV   120
AGKKMVVQST STGGDLGSNH FDLNIPGGGV GIFDGCTPQF GGLPGQRYGG ISSRNECDRF   180
PDALKPGCYW RFDWFKNADN PSFSFRQVQC PAELVARTGC RRNDDGNFPA VQIPSSSTSS   240
PVNQPTSTST TSTSTTSSPP VQPTTPSGCA DGRSTRYWDC CKPSCGWAKK APVNQPVFSC   300
NANFQRITDF DAKSGCEPGG VAYSCADQTP WAVNDDFALG FAATSIAGSN EAGWCCACYE   360
LTFTSGPVAG KKMVVQSTST GGDLGSNHFD LNIPGGGVGI FDGCTPQFGG LPGQRYGGIS   420
SRNECDRFPD ALKPGCYWRF DWFKNADNPS FSFRQVQCPA ELVARTGCRR             470

SEQ ID NO: 85           moltype = AA  length = 425
FEATURE                 Location/Qualifiers
source                  1..425
                        mol_type = protein
                        organism = Escherichia coli
SEQUENCE: 85
TALLLGLVNG QKPGETKEVH PQLTTFRCTK RGGCKPATNF IVLDSLSHPI HRAEGLGPGG    60
CGDWGNPPPK DVCPDVESCA KNCIMEGIPD YSQYGVTTNG TSLRLQHILP DGRVPSPRVY   120
LLDKTKRRYE MLHLTGFEFT FDVDATKLPC GMNSALYLSE MHPTGAKSKY NPGGAYYGTG   180
YCDAQCFVTP FINGLGNIEG KGSCCNEMDI WEANSRASHV APHTCNKKGL YLCEGEECAF   240
EGVCDKNGCG WNNYRVNVTD YYGRGEEFKV NTLKPFTVVT QFLANRRGKL EKIHRFYVQD   300
GKVIESFYTN KEGVPYTNMI DDEFCEATGS RKYMELGATQ GMGEALTRGM VLAMSIWWDQ   360
GGNMEWLDHG EAGPCAKGEG APSNIVQVEP FPEVTYTNLR WGEIGSTYQE VQKPKPKPGH   420
GPRSD                                                              425

SEQ ID NO: 86           moltype = AA  length = 773
FEATURE                 Location/Qualifiers
source                  1..773
                        mol_type = protein
                        organism = Bacillus subtilis
SEQUENCE: 86
AEGNTREDNF KHLLGNDNVK RPSEAGALQL QEVDGQMTLV DQHGEKIQLR GMSTHGLQWF    60
PEILNDNAYK ALANDWESNM IRLAMYVGEN GYASNPELIK SRVIKGIDLA IENDMYVIVD   120
WHVHAPGDPR DPVYAGAEDF FRDIAALYPN NPHIIYELAN EPSSNNNGGA GIPNNEEGWN   180
AVKEYADPIV EMLRDSGNAD DNIIIVGSPN WSQRPDLAAD NPINDHHTMY TVHFYTGSHA   240
ASTESYPPET PNSERGNVMS NTRYALENGV AVFATEWGTS QANGDGGPYF DEADVWIEFL   300
NENNISWANW SLTNKNEVSG AFTPFELGKS NATNLDPGPD HVWAPEELSL SGEYVRARIK   360
GVNYEPIDRT KYTKVLWDFN DGTKQGFGVN SDSPNKELIA VDNENNTLKV SGLDVSNDVS   420
DGNFWANARL SADGWGKSVD ILGAEKLTMD VIVDEPTTVA IAAIPQSSKS GWANPERAVR   480
VNAEDFVQQT DGKYKAGLTI TGEDAPNLKN IAFHEEDNNM NNIILFVGTD AADVIYLDNI   540
KVIGTEVEIP VVHDPKGEAV LPSVFEDGTR QGWDWAGESG VKTALTIEEA NGSNALSWEF   600
GYPEVKPSDN WATAPRLDFW KSDLVRGEND YVAFDFYLDP VRATEGAMNI NLVFQPPTNG   660
YWVQAPKTYT INFDELEEAN QVNGLYHYEV KINVRDITNI QDDTLLRNMM IIFADVESDF   720
AGRVFVDNVR FEGAATTEPV EPEPVDPGEE TPPVDEKEAK KEQKEAEKEE KEE          773

SEQ ID NO: 87           moltype = AA  length = 524
FEATURE                 Location/Qualifiers
source                  1..524
                        mol_type = protein
                        organism = Paenibacillus polymyxa
SEQUENCE: 87
VVHGQTAKTI TIKVDTFKDR KPISPYIYGT NQDLAGDENM AARRLGGNRM TGYNWENNMS    60
NAGSDWQHSS DNYLCSNGGL TQAECEKPGA VVTSFHDQSL KLGTYSLVTL PMAGYVAADG   120
NGSVQESEAA PSARWNQVVN AKNAPFQLQP DLNDNYYVYD EFVHFLVNKY GTASTKAGVK   180
GYALDNEPAL WSHTHPRIHP EKVGAKELVD RSVSLSKAVK AIDAGAEVFG PVLYGFGAYK   240
DLQTAPDWDS VKGNYSWFVD YYLDQMRLSS QVEGKRLLDV FDHWYPEAM GGGIRITNEV   300
GNDETKKARM QAPRTLWDPT YKEDSWIAQW FSEFLPILPR LKQSVDKYYP GTKLAMTEYS   360
YGGENDISGG IAMTDVLGIL GKNDVYMANY WKLKDGVNNY VSAAYKLYRN YDGKNSTFGD   420
TSVSAQTSDI VNSSVHASVT NASDKELHLV VMNKSMDSAF DAQFDLSGAK TYISGKVWGF   480
DKNSSQIKEA APITQISGNR FTYTVPPLTA YHIVLTTGND TSPV                   524

SEQ ID NO: 88           moltype = AA  length = 485
FEATURE                 Location/Qualifiers
```

```
source                  1..485
                        mol_type = protein
                        organism = Bacillus sp.
SEQUENCE: 88
HHNGTNGTMM QYFEWYLPND GNHWNRLRSD ASNLKDKGIS AVWIPPAWKG ASQNDVGYGA    60
YDLYDLGEFN QKGTIRTKYG TRNQLQAAVN ALKSNGIQVY GDVVMNHKGG ADATEMVRAV   120
EVNPNNRNQE VSGEYTIEAW TKFDFPGRGN THSNFKWRWY HFDGVDWDQS RKLNNRIYKF   180
RGDGKGWDWE VDTENGNYDY LMYADIDMDH PEVVNELRNW GVWYTNTLGL DGFRIDAVKH   240
IKYSFTRDWI NHVRSATGKN MFAVAEFWKN DLGAIENYLN KTNWNHSVFD VPLHYNLYNA   300
SKSGGNYDMR QIFNGTVVQR HPMHAVTFVD NHDSQPEEAL ESFVEEWFKP LAYALTLTRE   360
QGYPSVFYGD YYGIPTHGVP AMKSKIDPIL EARQKYAYGR QNDYLDHHNI IGWTREGNTA   420
HPNSGLATIM SDGAGGNKWM FVGRNKAGQV WTDITGNRAG TVTINADGWG NFSVNGGSVS   480
IWVNK                                                               485

SEQ ID NO: 89           moltype = AA length = 485
FEATURE                 Location/Qualifiers
source                  1..485
                        mol_type = protein
                        organism = Bacillus sp.
SEQUENCE: 89
HHNGTNGTMM QYFEWHLPND GNHWNRLRDD ASNLRNRGIT AIWIPPAWKG TSQNDVGYGA    60
YDLYDLGEFN QKGTVRTKYG TRSQLESAIH ALKNNGVQVY GDVVMNHKGG ADATENVLAV   120
EVNPNNRNQE ISGDYTIEAW TKFDFPGRGN TYSDFKWRWY HFDGVDWDQS RQFQNRIYKF   180
RGDGKAWDWE VDSENGNYDY LMYADVDMDH PEVVNELRRW GEWYTNTLNL DGFRIDAVKH   240
IKYSFTRDWL THVRNATGKE MFAVAEFWKN DLGALENYLN KTNWNHSVFD VPLHYNLYNA   300
SNSSGNYDMA KLLNGTVVQK HPMHAVTFVD NHDSQPGESL ESFVQEWFKP LAYALILTRE   360
QGYPSVFYGD YYGIPTHSVP AMKAKIDPIL EARQNFAYGT QHDYFDHHNI IGWTREGNTT   420
HPNSGLATIM SDGPGGEKWM YVGQNKAGQV WHDITGNKPG TVTINADGWA NFSVNGGSVS   480
IWVKR                                                               485

SEQ ID NO: 90           moltype = AA length = 485
FEATURE                 Location/Qualifiers
source                  1..485
                        mol_type = protein
                        organism = Bacillus sp.
SEQUENCE: 90
HHNGTNGTMM QYFEWYLPND GNHWNRLNSD ASNLKSKGIT AVWIPPAWKG ASQNDVGYGA    60
YDLYDLGEFN QKGTVRTKYG TRSQLQAAVT SLKNNGIQVY GDVVMNHKGG ADATEMVRAV   120
EVNPNNRNQE VTGEYTIEAW TRFDFPGRGN THSSFKWRWY HFDGVDWDQS RRLNNRIYKF   180
RGHGKAWDWE VDTENGNYDY LMYADIDMDH PEVVNELRNW GVWYTNTLGL DGFRIDAVKH   240
IKYSFTRDWI NHVRSATGKN MFAVAEFWKN DLGAIENYLQ KTNWNHSVFD VPLHYNLYNA   300
SKSGGNYDMR NIFNGTVVQR HPSHAVTFVD NHDSQPEEAL ESFVEEWFKP LAYALTLTRE   360
QGYPSVFYGD YYGIPTHGVP AMRSKIDPIL EARQKYAYGK QNDYLDHHNI LGWTREGNTA   420
HPNSGLATIM SDGAGGSKWM FVGRNKAGQV WSDITGNRTG TVTINADGWG NFSVNGGSVS   480
IWVNK                                                               485

SEQ ID NO: 91           moltype = AA length = 485
FEATURE                 Location/Qualifiers
REGION                  1..485
                        note = fusion protein
source                  1..485
                        mol_type = protein
                        organism = synthetic construct
SEQUENCE: 91
HHDGTNGTIM QYFEWNVPND GQHWNRLHNN AQNLKNAGIT AIWIPPAWKG TSQNDVGYGA    60
YDLYDLGEFN QKGTVRTKYG TKAELERAIR SLKANGIQVY GDVVMNHKGG ADFTERVQAV   120
EVNPQNRNQE VSGTYQIEAW TGFNPPGRGN QHSSFKWRWY HFDGTDWDQS RQLANRIYKF   180
RGDGKAWDWE VDTENGNYDY LMYADVDMDH PEVINELNRW GVWYANTLNL DGFRLDAVKH   240
IKFSFMRDWL GHVRGQTGKN LFAVAEYWKN DLGALENYLS KTNWTMSAFD VPLHYNLYNA   300
SNSSGNYDMR NLLNGTLVQR HPSHAVTFVD NHDTQPGEAL ESFVQGWFKP LAYATILTRE   360
QGYPQVFYGD YYGIPSDGVP SYRQQIDPLL KARQQYAYGT QHDYLDNQDV IGWTREGDSA   420
HAGSGLATVM SDGPGGSKTM YVGTAHAGQV FKDITGNRTD TVTINSAGNG TFPCNGGSVS   480
IWVKQ                                                               485
```

What is claimed is:

1. A cleaning composition comprising
(a) a DNase having at least 85% sequence identity to the polypeptide of SEQ ID NO: 13,
(b) a polypeptide having cellulase activity and at least 85% sequence identity to the polypeptide sequence of SEQ ID NO: 83, and
(c) a cleaning component.

2. The cleaning composition of claim 1, wherein
(a) the DNase has at least 90% sequence identity to the polypeptide of SEQ ID NO: 13; and
(b) the polypeptide having cellulase activity has at least 90% sequence identity to the polypeptide of SEQ ID NO: 83.

3. The cleaning composition of claim 1, wherein
(a) the DNase has at least 95% sequence identity to the polypeptide of SEQ ID NO: 13; and
(b) the polypeptide having cellulase activity has at least 95% sequence identity to the polypeptide of SEQ ID NO: 83.

4. The cleaning composition of claim 1, wherein
(a) the DNase has at least 97% sequence identity to the polypeptide of SEQ ID NO: 13; and (b) the polypeptide having cellulase activity has at least 97% sequence identity to the polypeptide of SEQ ID NO: 83.

5. The cleaning composition of claim 1, further comprising a mannanase.

6. The cleaning composition of claim 5, wherein the mannanase has at least 80% sequence identity to the polypeptide shown in SEQ ID NO: 82.

7. The cleaning composition of claim 1, further comprising an amylase.

8. The cleaning composition of claim 7, wherein the amylase is a polypeptide selected from the group consisting of:
- a polypeptide having at least 80% sequence identity to the polypeptide shown in SEQ ID NO: 88,
- a polypeptide having at least 80% sequence identity to the polypeptide shown in SEQ ID NO: 89,
- a polypeptide having at least 80% sequence identity to the polypeptide shown in SEQ ID NO: 90, and
- a polypeptide having at least 80% sequence identity to the polypeptide shown in SEQ ID NO: 91.

9. The cleaning composition of claim 1, further comprising a xylanase.

10. The cleaning composition of claim 9, wherein the xylanase has at least 80% sequence identity to the polypeptide shown in SEQ ID NO: 87.

11. The cleaning composition of claim 1, wherein the DNase comprises one or both of the motif(s) [D/M/L][S/T]GYSR[D/N] (SEQ ID NO: 73) or ASXNRSKG (SEQ ID NO: 74).

12. The cleaning composition of claim 1, wherein the amount of the DNase is from 0.01 to 1000 ppm and the amount of the polypeptide having cellulase activity is from 0.01 to 1000 ppm.

13. The cleaning composition of claim 1, wherein the cleaning component is a surfactant.

14. The cleaning composition of claim 13, wherein the surfactant is an anionic and/or nonionic surfactant.

15. The cleaning composition of claim 1, wherein the cleaning component is a builder or bleach component.

16. A kit for deep cleaning, which comprises a solution of a mixture comprising
(a) a DNase having DNA activity and at least 85% sequence identity to the polypeptide of SEQ ID NO:13,
(b) a polypeptide having cellulase activity and at least 85% sequence identity to the polypeptide of SEQ ID NO: 83, and
(c) a cleaning component.

17. A method of deep cleaning a textile, comprising washing the textile with a cleaning composition of claim 1.

* * * * *